(12) United States Patent
Pebay et al.

(10) Patent No.: US 7,604,990 B2
(45) Date of Patent: Oct. 20, 2009

(54) METHODS OF REGULATING DIFFERENTIATION IN STEM CELLS

(75) Inventors: Alice Marie Pebay, Melbourne (AU); Martin Frederick Pera, Prahran (AU)

(73) Assignee: ES Cell International Pte Ltd., Singapore ( * ) Notice: Subject to any disclaimer, the term of this patent is extended or adjusted under 35 U.S.C. 154(b) by 524 days.

(21) Appl. No.: 11/006,300

(22) Filed: Dec. 7, 2004

(65) Prior Publication Data
US 2005/0266553 A1    Dec. 1, 2005

Related U.S. Application Data

(63) Continuation of application No. PCT/AU03/00713, filed on Jun. 6, 2003.

(30) Foreign Application Priority Data

| Jun. 7, 2002 | (AU) | ............... PS2860 |
| Jun. 7, 2002 | (AU) | ............... PS2861 |
| Mar. 21, 2003 | (AU) | ............... 2003901313 |
| Jun. 2, 2003 | (AU) | ............... 2003902729 |

(51) Int. Cl.
*C12N 5/00* (2006.01)
*C12N 5/06* (2006.01)
*C12N 5/08* (2006.01)

(52) U.S. Cl. ............. 435/325; 435/377; 435/354; 435/365

(58) Field of Classification Search ............... None
See application file for complete search history.

(56) References Cited

U.S. PATENT DOCUMENTS

| 6,150,345 A | * | 11/2000 | Chun et al. ............... 514/120 |
| 6,566,096 B2 | * | 5/2003 | Munroe et al. ............... 435/69.1 |
| 2004/0014662 A1 | * | 1/2004 | Lindquist et al. ............... 514/12 |

FOREIGN PATENT DOCUMENTS

| WO | WO 01/11011 | 2/2001 |
| WO | WO 03/051395 | 6/2003 |
| WO | WO 03/062252 | 7/2003 |
| WO | WO 03/074008 | 9/2003 |
| WO | WO 03/097028 | 11/2003 |

OTHER PUBLICATIONS

Yanai et al., Blood, vol. 96 No. 1 Jul. 1, 2000: pp. 139-144.*
Harada, J. et al., "Sphingosine-1-phosphate induces proliferation and morphological changes of neural progenitor cells", BIOSIS, XP002260727, (2001), Abstract.
Bathurst, I. C. et al., "Soy (*Glycine Max*)-Derived Phospholipids Exhibit Potent Anti-Apoptotic Activity", *Pharmaceutical Biology* 36(2): 111-123 (1998).
Nam, J. S. et al., "Survival of hippocampal neuroprogenitor cells by lysophosphatidic acid involves activation of cyclic AMP-response element binding protein", BIOSIS, XP002260728, (2001), Abstract.
Pease, S. et al., "Isolation Of Embryonic Stem (ES) Cells In Media Supplemented With Recombinant Leukemia Inhibitory Factor (LIF)", *Developmental Biology* 141: 344-352.
Tang et al., "Long-Term Culture of Purified Postnatal Oligodendrocyte Precursor Cells: Evidence For An Instrinsic Maturation Program That Plays Out Over Months", *The Journal of Cell Biology*, vol. 148(5): 971-984 (2000).
Erlandsson et al., "Imature Neurons From CNS Stem Cell Proliferate In Response to Platelet-Derived Growth Factor", *The Journal of Neuroscience*, vol. 21(10): 3483-3491 (2001).
Tang et al., "Long-Term Culture of Purified Postnatal Oligodendrocyte Precursor Cells: Evidence For An Instrinsic Maturation Program That Plays Out Over Months", *The Journal of Cell Biology*, vol. 148(5):971-984 (2000).
Erlandsson et al., "Imature Neurons From CNS Stem Cells Proliferative In Response to Platelet-Derived Growth Factor", *The Journal of Neuroscience*, vol. 21(10): 3483-3491 (2001).
Lee et al., Sphingosine-1-Phosphate As A Ligand For The G Protein-Coupled Receptor EDG-1), *Science*, vol. 279: 1552-1555 (1998).

* cited by examiner

*Primary Examiner*—Daniel C Gamett
(74) *Attorney, Agent, or Firm*—Scully, Scott, Murphy & Presser, P.C.

(57) ABSTRACT

The present invention provides methods, media and compositions capable of modulating the differentiation of stem cells. Applicants have discovered that agonists of lysophospholipid receptors and ligands of class III tyrosine kinase receptors are useful in preventing the spontaneous differentiation of stem cells. The ligands and agonists may be used alone, or in combination where they have a synergistic effect. Also provided are cells produced using the methods and media, and methods of treating stem cell related diseases using the compositions described herein. Methods of identifying compounds useful in finding other agents useful in the modulation of stem cell differentiation are also disclosed.

25 Claims, 11 Drawing Sheets

SEQUENCE LISTING

<160> NUMBER OF SEQ ID NOS: 44

<210> SEQ ID NO 1
<211> LENGTH: 20
<212> TYPE: DNA
<213> ORGANISM: Homo sapiens

<400> SEQUENCE: 1
ccacaacggg agcaataact                                         20

<210> SEQ ID NO 2
<211> LENGTH: 20
<212> TYPE: DNA
<213> ORGANISM: Homo sapiens

<400> SEQUENCE: 2
gtaaatgatg gggttggtgc                                         20

<210> SEQ ID NO 3
<211> LENGTH: 22
<212> TYPE: DNA
<213> ORGANISM: Homo sapiens

<400> SEQUENCE: 3
ccaatacctt gctctctctg gc                                      22

<210> SEQ ID NO 4
<211> LENGTH: 20
<212> TYPE: DNA
<213> ORGANISM: Homo sapiens

<400> SEQUENCE: 4
cagaaggagg atgctgaagg                                         20

<210> SEQ ID NO 5
<211> LENGTH: 20
<212> TYPE: DNA
<213> ORGANISM: Homo sapiens

<400> SEQUENCE: 5
tcagggaggg cagtatgttc                                         20

<210> SEQ ID NO 6
<211> LENGTH: 20
<212> TYPE: DNA
<213> ORGANISM: Homo sapiens

<400> SEQUENCE: 6
ctgagccttg aagaggatgg                                         20

<210> SEQ ID NO 7
<211> LENGTH: 20
<212> TYPE: DNA
<213> ORGANISM: Homo sapiens

<400> SEQUENCE: 7
cggctcattg ttctgcacta                                         20

<210> SEQ ID NO 8
<211> LENGTH: 20
<212> TYPE: DNA
<213> ORGANISM: Homo sapiens

-continued

<400> SEQUENCE: 8
gatcatcagc accgtcttca                                        20

<210> SEQ ID NO 9
<211> LENGTH: 20
<212> TYPE: DNA
<213> ORGANISM: Homo sapiens

<400> SEQUENCE: 9
ttctgatacc agagtccggg                                        20

<210> SEQ ID NO 10
<211> LENGTH: 20
<212> TYPE: DNA
<213> ORGANISM: Homo sapiens

<400> SEQUENCE: 10
caaggcctac gtgctcttct                                        20

<210> SEQ ID NO 11
<211> LENGTH: 23
<212> TYPE: DNA
<213> ORGANISM: Homo sapiens

<400> SEQUENCE: 11
gctccacaca cggatgagca acc                                    23

<210> SEQ ID NO 12
<211> LENGTH: 24
<212> TYPE: DNA
<213> ORGANISM: Homo sapiens

<400> SEQUENCE: 12
gtggtcattg ctgtgaactc cagc                                   24

<210> SEQ ID NO 13
<211> LENGTH: 23
<212> TYPE: DNA
<213> ORGANISM: Homo sapiens

<400> SEQUENCE: 13
agctgcacag ccgcctgccc cgt                                    23

<210> SEQ ID NO 14
<211> LENGTH: 24
<212> TYPE: DNA
<213> ORGANISM: Homo sapiens

<400> SEQUENCE: 14
tgctgtgcca tgccagacct tgtc                                   24

<210> SEQ ID NO 15
<211> LENGTH: 24
<212> TYPE: DNA
<213> ORGANISM: Homo sapiens

<400> SEQUENCE: 15
ccatagcaac ctgaccaaaa agag                                   24

<210> SEQ ID NO 16
<211> LENGTH: 24
<212> TYPE: DNA

-continued

<213> ORGANISM: Homo sapiens

<400> SEQUENCE: 16
tccttgtagg agtagatgat gggg                                          24

<210> SEQ ID NO 17
<211> LENGTH: 20
<212> TYPE: DNA
<213> ORGANISM: Homo sapiens

<400> SEQUENCE: 17
atcaatcagc ccagatggac                                               20

<210> SEQ ID NO 18
<211> LENGTH: 20
<212> TYPE: DNA
<213> ORGANISM: Homo sapiens

<400> SEQUENCE: 18
ttcacgggca gaaaggtact                                               20

<210> SEQ ID NO 19
<211> LENGTH: 20
<212> TYPE: DNA
<213> ORGANISM: Homo sapiens

<400> SEQUENCE: 19
aatgtctcca gcaccttcgt                                               20

<210> SEQ ID NO 20
<211> LENGTH: 20
<212> TYPE: DNA
<213> ORGANISM: Homo sapiens

<400> SEQUENCE: 20
agcggatgtg gtaaggcata                                               20

<210> SEQ ID NO 21
<211> LENGTH: 20
<212> TYPE: DNA
<213> ORGANISM: Homo sapiens

<400> SEQUENCE: 21
cagaacctgc tgcctgaatg                                               20

<210> SEQ ID NO 22
<211> LENGTH: 21
<212> TYPE: DNA
<213> ORGANISM: Homo sapiens

<400> SEQUENCE: 22
gtagaaatgc ctgaggaaac g                                             21

<210> SEQ ID NO 23
<211> LENGTH: 20
<212> TYPE: DNA
<213> ORGANISM: Homo sapiens

<400> SEQUENCE: 23
acccatgaac ctgctgtctc                                               20

<210> SEQ ID NO 24
<211> LENGTH: 20

```
<212> TYPE: DNA
<213> ORGANISM: Homo sapiens

<400> SEQUENCE: 24
caggtgtctt ggaacccact                                              20

<210> SEQ ID NO 25
<211> LENGTH: 19
<212> TYPE: DNA
<213> ORGANISM: Homo sapiens

<400> SEQUENCE: 25
tggcagtggt gtaagaacc                                               19

<210> SEQ ID NO 26
<211> LENGTH: 19
<212> TYPE: DNA
<213> ORGANISM: Homo sapiens

<400> SEQUENCE: 26
cagtcagggc gatctagga                                               19

<210> SEQ ID NO 27
<211> LENGTH: 22
<212> TYPE: DNA
<213> ORGANISM: Homo sapiens

<400> SEQUENCE: 27
cgttctcttt ggaaaggtgt tc                                           22

<210> SEQ ID NO 28
<211> LENGTH: 20
<212> TYPE: DNA
<213> ORGANISM: Homo sapiens

<400> SEQUENCE: 28
acactcggac cacgtctttc                                              20

<210> SEQ ID NO 29
<211> LENGTH: 20
<212> TYPE: DNA
<213> ORGANISM: Homo sapiens

<400> SEQUENCE: 29
ccacaacggg agcaataact                                              20

<210> SEQ ID NO 30
<211> LENGTH: 20
<212> TYPE: DNA
<213> ORGANISM: Homo sapiens

<400> SEQUENCE: 30
gtaaatgatg gggttggtgc                                              20

<210> SEQ ID NO 31
<211> LENGTH: 20
<212> TYPE: DNA
<213> ORGANISM: Homo sapiens

<400> SEQUENCE: 31
tcagggaggg cagtatgttc                                              20

<210> SEQ ID NO 32
```

-continued

```
<211> LENGTH: 20
<212> TYPE: DNA
<213> ORGANISM: Homo sapiens

<400> SEQUENCE: 32
ctgagccttg aagaggatgg                                                   20

<210> SEQ ID NO 33
<211> LENGTH: 22
<212> TYPE: DNA
<213> ORGANISM: Homo sapiens

<400> SEQUENCE: 33
ccaatacctt gctctctctg gc                                                22

<210> SEQ ID NO 34
<211> LENGTH: 20
<212> TYPE: DNA
<213> ORGANISM: Homo sapiens

<400> SEQUENCE: 34
cagaaggagg atgctgaagg                                                   20

<210> SEQ ID NO 35
<211> LENGTH: 20
<212> TYPE: DNA
<213> ORGANISM: Homo sapiens

<400> SEQUENCE: 35
cggctcattg ttctgcacta                                                   20

<210> SEQ ID NO 36
<211> LENGTH: 20
<212> TYPE: DNA
<213> ORGANISM: Homo sapiens

<400> SEQUENCE: 36
gatcatcagc accgtcttca                                                   20

<210> SEQ ID NO 37
<211> LENGTH: 20
<212> TYPE: DNA
<213> ORGANISM: Homo sapiens

<400> SEQUENCE: 37
ttctgatacc agagtccggg                                                   20

<210> SEQ ID NO 38
<211> LENGTH: 20
<212> TYPE: DNA
<213> ORGANISM: Homo sapiens

<400> SEQUENCE: 38
caaggcctac gtgctcttct                                                   20

<210> SEQ ID NO 39
<211> LENGTH: 23
<212> TYPE: DNA
<213> ORGANISM: Homo sapiens

<400> SEQUENCE: 39
gctccacaca cggatgagca acc                                               23
```

```
<210> SEQ ID NO 40
<211> LENGTH: 24
<212> TYPE: DNA
<213> ORGANISM: Homo sapiens

<400> SEQUENCE: 40
gtggtcattg ctgtgaactc cagc                                          24

<210> SEQ ID NO 41
<211> LENGTH: 23
<212> TYPE: DNA
<213> ORGANISM: Homo sapiens

<400> SEQUENCE: 41
agctgcacag ccgcctgccc cgt                                           23

<210> SEQ ID NO 42
<211> LENGTH: 24
<212> TYPE: DNA
<213> ORGANISM: Homo sapiens

<400> SEQUENCE: 42
tgctgtgcca tgccagacct tgtc                                          24

<210> SEQ ID NO 43
<211> LENGTH: 24
<212> TYPE: DNA
<213> ORGANISM: Homo sapiens

<400> SEQUENCE: 43
ccatagcaac ctgaccaaaa agag                                          24

<210> SEQ ID NO 44
<211> LENGTH: 24
<212> TYPE: DNA
<213> ORGANISM: Homo sapiens

<400> SEQUENCE: 44
tccttgtagg agtagatgat gggg                                          24
```

METHODS OF REGULATING DIFFERENTIATION IN STEM CELLS

CROSS-REFERENCE TO RELATED APPLICATIONS

Figure 1:
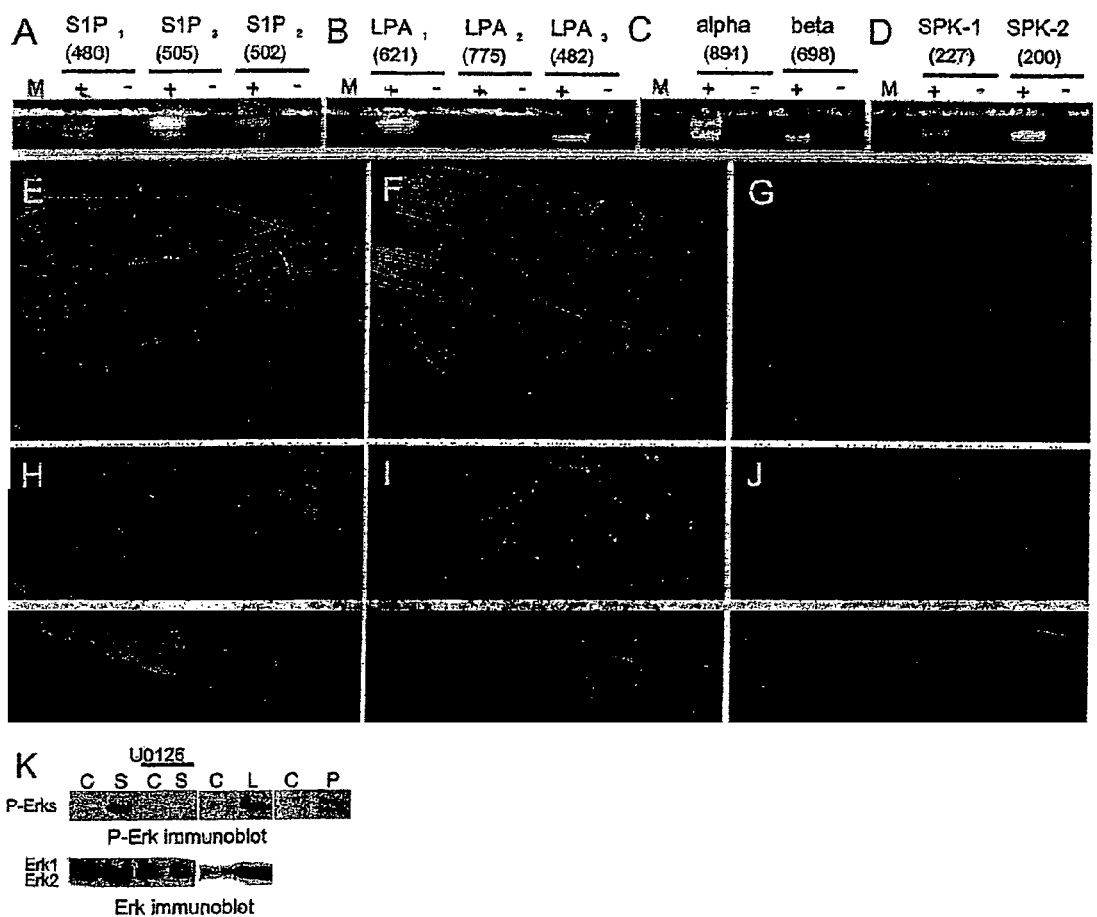

The present application is a continuation of PCT/AU03/00713, filed Jun. 6, 2003.

TECHNICAL FIELD

The present invention relates to methods for inhibiting spontaneous differentiation of stem cells. The invention also relates to media useful in propagating stem cells in an undifferentiated state, methods for identifying agents useful for inhibiting stem cell differentiation, and methods of treating stem cell related disorders.

BACKGROUND ART

In general, stem cells are undifferentiated cells which can give rise to a succession of mature functional cells. For example, a haematopoietic stem cell may give rise to any of the different types of terminally differentiated blood cells. Embryonic stem (ES) cells are derived from the embryo and are pluripotent, thus possessing the capability of developing into any organ, cell type or tissue type or, at least potentially, into a complete embryo. ES cells may be derived from the inner cell mass of the blastocyst, which have the ability to differentiate into tissues representative of the three embryonic germ layers (mesoderm, ectoderm, endoderm), and into the extra-embryonic tissues that support development.

Human embryonic stem cells (hES cells) are pluripotent cell lines derived from the inner cell mass of the blastocyst. These cells have the ability to differentiate into functional tissues representative of the three embryonic germ layers (mesoderm, ectoderm, endoderm), and into extra-embryonic tissues that support development. Because of their ability to generate these different cellular fates, hES cells are considered to be of great potential for future therapies.

However, during routine culture in vitro, established hES cell lines have a tendency to spontaneously differentiate. Because the pluripotency of these cells is associated with their undifferentiated state, it is desirable to find a way to limit this spontaneous differentiation. Contrary to what is seen in mouse embryonic stem cells, leukemia inhibitory factor (LIF) does not prevent the spontaneous differentiation of hES cells [1]. Thus, a common way to grow and then to maintain hES cells in an optimum state is to cultivate them on feeder layers, which are constituted by primary mouse embryonic fibroblasts (MEF), in media supplemented with high doses of foetal calf serum.

However, serum contains a wide variety of biologically active compounds that might have the potential to adversely affect hES cell growth and differentiation. Furthermore, there is a biosafety issue if cells cultured in animal serum are subsequently used for implantation in a human or for the production of a biological therapeutic.

With regard to these issues and in order to establish a serum-free culture system to grow hES cells, it is of great importance to identify the specific factors in serum that are responsible for its beneficial effect on the growth of hES cells. Thus, alternative approaches to traditional culture systems are desirable, such as the use of a serum replacement medium such as Knockout Serum Replacement [2, 3].

Sphingosine-1-phosphate (S1P) and lysophosphatidic acid (LPA) are two small bioactive lysophospholipids, present in serum (at concentration of up to 1 and 5 µM respectively) [4], released by activated platelets, which act on a wide range of cell types derived from the three developmental germ layers. Most of the effects of these lysophospholipids seem to be mediated by specific lysophospholipid G-protein coupled receptors (LPL receptors) previously named endothelial differentiation gene (Edg) receptors.

Up to now, eight distinct mammalian LPL/Edg receptors have been identified: $S1P_1$/Edg-1, $S1P_2$/Edg-5, $S1P_3$/Edg-3, $S1P_4$/Edg-6 and $S1P_5$/Edg-8 are specific for S1P while $LPA_1$/Edg-2, $LPA_2$/Edg-4 and $LPA_3$/Edg-7 are specific for LPA (for reviews see [5, 6]). Each of these receptors is coupled to at least one G protein and can activate or inhibit specific signalling pathways. For instance, all these receptors are coupled to $G_{i/o}$ proteins (for review see [5, 6]).

By activating notably these $G_{i/o}$ proteins, S1P and LPA can stimulate the extracellular-signal-regulated kinases 1 and 2 (ERK1/2), which are members of the mitogen-activated protein (MAP) kinase family, and thus are involved in regulation of major cellular events, such as cell proliferation or differentiation. S1P and LPA are potent biological agents involved in numerous cell events, such as proliferation, differentiation, death or migration (for review see [5]) since the very early stages of development.

S1P stimulates mammalian angiogenesis, at least via $S1P_1$ and $S1P_2$ [7-10]. Thus, $S1P_1$ knockout mice show impaired blood vessel maturation. Moreover, in the zebrafish, S1P is required for normal heart development [11]. Thus, in these animals, the mutation of the gene mil that encodes the S1P receptor Mil (very similar to the mammalian $S1P_2$ receptor) impairs migration of cardiac progenitor cells [11].

On the other hand, LPA seems to be mainly involved in neurogenesis [12]. For instance, LPA, probably via $LPA_1$, stimulates cell cycle-morphological changes and cell migration of cultured cortical neuroblasts. Moreover, LPA, probably via $LPA_2$, regulates the migration of post-mitotic neurons to their final destination. Last but not least, $LPA_1$ knockout mice present abnormal cerebral cortices and olfactory bulbs, probably due to impaired development, demonstrating $LPA_1$ is essential for a normal brain development [13].

Within serum, Platelet-Derived Growth Factor (PDGF) is a major protein growth factor that has been widely described as a potent mitogen of numerous kinds of cells. PDGF has also been shown to induce chemotaxis, actin re-organization, and to prevent apoptosis. This growth factor belongs to a family of dimeric isoforms of polypeptide chains, A, B, C and D that act through different tyrosine kinase receptors: PDGFR-α and PDGFR-β.

S1P and PDGF have additional effects that induce biological responses. Thus S1P and PDGF are able to regulate smooth muscle cell migration, proliferation and vascular maturation. Moreover, Hobson et al. (2001), and Rosenfeld et al. (2001) demonstrated that PDGF-stimulated cell motility is $S1P_1$-dependent in HEK 293 cells and MEF [14, 15] while Kluk et al. (2003) showed that this effect was independent of $S1P_1$ in vascular smooth muscles and MEF [16]. Last but not least, it is now proposed that PDGF is able to stimulate the enzyme sphingosine kinase, which leads to an increase in S1P intracellular concentration [17], an effect that would be responsible for PDGF-induced proliferation in Swiss 3T3 cells [17] and vascular smooth muscle cells [18].

The discussion of documents, acts, materials, devices, articles and the like is included in this specification solely for the purpose of providing a context for the present invention. It is not suggested or represented that any or all of these matters formed part of the prior art base or were common general

SUMMARY OF THE INVENTION

In one aspect the present invention provides a method for modulating spontaneous differentiation of a stem cell, which method comprises incubating the stem cell in the presence of an agonist of a LPL receptor and/or a ligand of a class III tyrosine kinase receptor.

In another aspect the present invention provides a serum free or substantially serum free medium useful for modulating spontaneous differentiation of a stem cell, comprising an agonist of a LPL receptor and/or a ligand of a class III tyrosine kinase receptor.

Another aspect of the present invention provides a method of treating or preventing a disorder of stem cell differentiation comprising administering to an animal in need thereof a composition containing an agonist of a LPL receptor and/or a ligand of a class III tyrosine kinase receptor.

Another aspect of the present invention provides a pharmaceutical composition comprising a class III tyrosine kinase receptor ligand and/or a LPL receptor agonist.

In a further aspect the present invention provides a method of producing a population of proliferating undifferentiated stem cells from a stem cell which method comprises incubating the stem cell in the presence of an agonist of the LPL receptor and/or a ligand of a class III tyrosine kinase receptor In another aspect the present invention provides a method of producing a population of proliferating undifferentiated stem cells from a stem cell which method comprises incubating the stem cell in the presence of an agonist of the LPL receptor and/or a ligand of a class III tyrosine kinase receptor.

DESCRIPTION OF THE INVENTION

The present inventors investigated the role of the LPL receptor agonists S1P, dihydro S1P and LPA, and the ligand of a class III tyrosine kinase receptor, PDGF, in modulating the fate of hES cells in culture.

The present inventors have established that hES cells are target cells for S1P, dihydro S1P, LPA and PDGF, through expression of the LPL receptors, PDGFR-α and PDGFR-β and through stimulation of ERKs by these agonists. Moreover the present inventors have found that S1P and PDGF slightly inhibit the spontaneous differentiation of hES cells while co-incubation with both S1P and PDGF strongly reduces the spontaneous differentiation of hES cells. These findings provide a basis for the establishment of a serum-free culture medium for stem cells and in particular hES cells.

Throughout the description and claims of this specification, the word "comprise" and variations of that word, such as "comprising" and "comprises" are not intended to exclude other additives, steps or integers.

In a first aspect the present invention provides a method for modulating spontaneous differentiation of a stem cell, which method comprises incubating the stem cell in the presence of an agonist of a LPL receptor.

In a second aspect the present invention provides a method for modulating spontaneous differentiation of a stem cell, which method comprises incubating the stem cell in the presence of a ligand of a class III tyrosine kinase receptor.

In a third aspect the present invention provides a method for modulating spontaneous differentiation of a stem cell, which method comprises incubating the stem cell in the presence of an agonist of a LPL receptor and a ligand of a class III tyrosine kinase receptor.

Sphingosine-1-phosphate (S1P), an agonist of the LPL receptors has the ability to at least partially inhibit the spontaneous loss of stem cell phenotype in cell culture. It has also been found that the method does not affect the ability of stem cells to proliferate.

Preferably, the LPL receptor is selected from the group consisting of S1P1, S1P2 and S1P3.

As used herein the term "modulating the differentiation of a stem cell" includes the inhibition or enhancement of cellular differentiation. The term also includes partial inhibition or enhancement of cellular differentiation. In a preferred form of the method, the modulation is inhibition of differentiation.

Typically the agonist is a phospholipid.

As used herein, the term "phospholipid" refers to a molecule that includes a backbone attached to two fatty acid moieties and a phosphate group. The backbone on which the fatty acid molecules are attached is variable and may be based on glycerol or sphingosine for example.

The term "lysophospholipid" refers to a phospholipid molecule where one of the fatty acid chains has been removed. The removal of a fatty acid chain may be accomplished by treatment of the phospholipid with an enzyme such as phospholipidase A2.

The phospholipid or lysophoholipid may have a sphingosine backbone, and particularly, the lysophospholipid may be a phosphorlyated amino alcohol. Preferably the agonist is selected from the group consisting of S1P, dihydro S1P, LPA, PAF and SPC or functional equivalents thereof.

In a highly preferred form of the invention the lysophospholipid is sphingosine-1-phosphate (S1P) or a functional equivalent thereof. S1P is a small bioactive phospholipid, present in serum, released by activated platelets, which has the following structure:

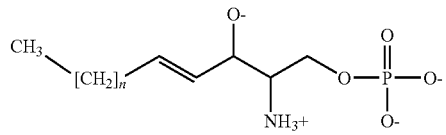

The skilled person will understand that bioactive molecules such as phospholipids and lysophospholipids may be altered in a number of ways and still retain biological activity. Accordingly, the scope of the present invention includes altered forms of phospholipids and lysopholipids that retain their LPL receptor agonist activity. The scope of the present invention also includes synthetic peptidic agonists of the LPL receptors.

The skilled person will be familiar with methods which can be applied to testing phospholipids or lysophospholipids for the ability to modulate the ability of a stem cell to differentiate. Suitable methods are found herein, and include reactivity with antibodies such as GCTM-2 which are directed to stem cell specific markers, and simple morphological evaluation of cells by light microscopy.

For example, the effect of the agonist on the differentiation of stem cells into neuronal or endodermal lineages may be studies by analysis of marker expression as shown in PCT/AU01/00278 and PCT/AU01/00735.

The phospholipid or lysophospholipid may be extracted from a biological source such as serum. In addition, mast cells and monocytes are able to produce S1P while adipocytes produce LPA, however the main source of LPA and S1P is activated platelets. Alternatively, the phospholipid may be synthesised by procedures well known in the field of organic chemistry.

Preferably, cells that have been exposed to a LPL receptor agonist are not substantially negatively affected in their ability to proliferate. Therefore, an advantage of the methods and compositions described herein is that it is possible to expand a population of hES cells without leading to a loss in pluripotency. Methods for determining the proliferative capability of a hES cell will be known by the skilled person and include detection of the cell proliferation marker PCNA as described herein.

Typically the ligand is a PDGF or functional equivalent thereof.

The tyrosine kinase receptor may be PDGFR-α or PDGFR-β.

In a preferred embodiment the PDGF is PDGFaa, PDGFab or PDGFbb which bind to the two types of receptors.

The method may also include use of TNF alpha, NGF (nerve growth factor), muscarinic acetylcholine agonists, serum or phorbol esters—which again are compounds that have additive or synergistic effects with S1P in other cell types.

The stem cell may be derived from foetal tissue or adult tissue.

The stem cell is typically an ES cell. Preferably the stem cell is a hES cell. As used herein the term "embryonic stem cell" means a cultured cell line derived from preimplantation stages of development capable of differentiation into tissues representative of all three embryonic germ layers.

Theses cells:
express SSEA-3,SSEA-4, TRA 1-60, GCTM-2, alkaline phosphatase and Oct-4
Grow as flat colonies with distinct cell borders
Differentiate into derivatives of all three embryonic germ layers
Are feeder cell dependent (feeder cell effect on growth not reconstituted by conditioned medium from feeder cells or by feeder cell extracellular matrix)
Are highly sensitive to dissociation to single cells and show poor cloning efficiency even on a feeder cell layer
Do not respond to Leukemia Inhibitory Factor In a fourth aspect the present invention provides a serum free medium useful for modulating spontaneous differentiation of a stem cell having a LPL receptor, comprising an agonist of the LPL receptor and a ligand of a class III tyrosine kinase receptor.

In a fifth aspect the present invention provides a serum free medium useful for modulating spontaneous differentiation of a stem cell, comprising a ligand of a class III tyrosine kinase receptor.

The medium is useful in propagating stem cells such as human embryonic stem cells in an undifferentiated state.

Typically the ligand is a PDGF or functional equivalent thereof.

The tyrosine kinase receptor may be PDGFR-α or PDGFR-β.

In a preferred embodiment the PDGF is PDGFaa, PDGFab or PDGFbb.

The medium may also include TNF alpha, NGF (nerve growth factor), muscarinic acetylcholine agonists, serum or phorbol esters—which again are compounds that have additive or synergistic effects with S1P.

Typically the agonist is a phospholipid.

Preferably the agonist is selected from the group consisting of S1P, LPA, PAF, dihydro S1P and SPC or functional equivalents thereof.

The stem cells may be derived from foetal tissue or adult tissue.

The stem cells are typically embryonic stem cells.

Preferably the stem cells are from embryonic tissue.

Typically the stem cells are of human origin.

The base medium is typically a standard serum free medium that is supplemented with phospholipids and ligand as well as a buffering agent. A suitable buffering agent is 25 mM Hepes.

The medium is of use in inhibiting the differentiation of pluripotent stem cells.

The cell culture medium may be based on any of the base media known in the art useful for the growth and/or maintenance of stem cells such as hES cells. Such media include but are not limited to Dulbecco's Modified Eagles Medium (DMEM), KNOCKOUT-DMEM or hES medium. In a preferred form of the invention the medium is based on DMEM supplemented with insulin, transferrin and selenium.

The optimal concentration of LPL agonist in the medium may be determined by routine experimentation. However, in a preferred form of the invention the agonist is present in the medium at a concentration of from 0.1 μM to 10 μM where the agonist is S1P. In a highly preferred form of the invention the agonist is present in the medium at a concentration of about 10 μM. It would be expected that the optimum concentration will vary according to a number of parameters including the species of agonist, the line of stem cells being cultured, the base medium used, and other culture conditions such as temperature, carbon dioxide concentration, and humidity.

The optimal concentration of ligand in the medium may be determined by routine experimentation. However, in a preferred form of the invention the ligand is present in the medium at a concentration of from 1 ng/ml to 20 ng/ml where the ligand is PDGFaa, PDGFab or PDGFbb. In a highly preferred form of the invention the ligand is present in the medium at a concentration of 20 ng/ml. Again, it would be expected that the optimum concentration will vary according to a number of parameters including the species of agonist, the line of stem cells being cultured, the base medium used, and other culture conditions such as temperature, carbon dioxide concentration, and humidity.

The skilled person understands that it is often necessary to culture hES cells on feeder cells, and the present invention contemplates methods including the use of such feeder cells. The concentration of agonist may also need to be optimised according to the feeder cell line used.

In a fifth aspect the present invention provides a stem cell grown and/or maintained in a cell culture medium of the invention.

Cells of the present invention will find many uses in biology and medicine. The properties of pluripotentiality and immortality are unique to ES cells and enable investigators to approach many issues in human biology and medicine for the first time. ES cells potentially can address the shortage of donor tissue for use in transplantation procedures, particularly where no alternative culture system can support growth of the required committed stem cell. However, it must be noted that almost all of the wide ranging potential applications of ES cell technology in human medicine-basic embryological research, functional genomics, growth factor and drug discovery, toxicology, and cell transplantation are based on the assumption that it will be possible to increase the proliferation and therefore grow ES cells on a large scale, to introduce genetic modifications into them, and to direct their differentiation.

The present invention provides a method of producing a population of proliferating undifferentiated stem cells from a stem cell which method comprises incubating the stem cell in the presence of an agonist of the LPL receptor and a ligand of a class III tyrosine kinase receptor.

The present invention also provides a method of producing a population of proliferating undifferentiated stem cells from a stem cell which method comprises incubating the stem cell in the presence of a ligand of a class III tyrosine kinase receptor.

The present invention further provides a method of producing a population of proliferating undifferentiated stem cells from a stem cell which method comprises incubating the stem cell in the presence of an agonist of the LPL receptor.

These methods therefore provide for the expansion of stem cell populations.

The invention also provides a population of undifferentiated stem cells produced by at least one of these methods.

Preferably, the LPL receptor is selected from the group consisting of S1P1, S1P2 and S1P3.

Typically the agonist is a phospholipid.

Preferably the agonist is selected from the group consisting of S1P, dihydro S1P, LPA, PAF and SPC or functional equivalents thereof. In a highly preferred form of the invention the lysophospholipid is sphingosine-1-phosphate (S1P) or a functional equivalent thereof.

Typically the ligand is a PDGF or functional equivalent thereof.

The tyrosine kinase receptor may be PDGFR-α or PDGFR-β.

In a preferred embodiment the PDGF is PDGFaa, PDGFab or PDGFbb which bind to the two types of receptors.

The ligand may also be TNF alpha, NGF (nerve growth factor), muscarinic acetylcholine agonists, serum or phorbol esters.

The stem cell may be derived from foetal tissue or adult tissue.

The stem cell is typically an ES cell. Preferably the stem cell is a hES cell.

Another aspect of the present invention is a method of treating or preventing a disorder of stem cell differentiation comprising administering to an animal in need thereof a composition containing an agonist of a LPL receptor. Methods for the preparation of pharmaceutical compositions are well known in the art, as set out in textbooks such as Remington's Pharmaceutical Sciences, 18$^{th}$ Edition, Mack Publishing Company, Easton, Pa., USA, the contents of which is incorporated herein.

The present invention also provides a method of treating or preventing a disorder of stem cell differentiation comprising administering to an animal in need thereof a composition containing an agonist of a LPL recepetor.

The present invention also provides a method of treating or preventing a disorder of stem cell differentiation comprising administering to an animal in need thereof a composition containing a ligand of a class III tyrosine kinase receptor.

Another aspect of the present invention is a method of treating or preventing a disorder of stem cell differentiation comprising administering to an animal in need thereof a composition containing an agonist of a LPL receptor and a ligand of a class III tyrosine kinase receptor.

The present invention also provides a method of treating or preventing a disorder of stem cell differentiation comprising administering a stem cell as described herein. Disorders of stem cell differentiation are well known to those skilled in the art, and include, but are not limited to the following:

Acute Leukemias

Acute Lymphoblastic Leukemia (ALL)

Acute Myelogenous Leukemia (AML)

Acute Biphenotypic Leukemia

Acute Undifferentiated Leukemia

Chronic Leukemias

Chronic Myelogenous Leukemia (CML)

Chronic Lymphocytic Leukemia (CLL)

Juvenile Chronic Myelogenous Leukemia (JCML)

Juvenile Myelomonocytic Leukemia (JMML)

Myelodysplastic Syndromes

Refractory Anemia (RA)

Refractory Anemia with Ringed Sideroblasts (RARS)

Refractory Anemia with Excess Blasts (RAEB)

Refractory Anemia with Excess Blasts in Transformation (RAEB-T)

Chronic Myelomonocytic Leukemia (CMML)

Stem Cell Disorders

Aplastic Anemia (Severe)

Fanconi Anemia

Paroxysmal Nocturnal Hemoglobinuria (PNH)

Pure Red Cell Aplasia

Myeloproliferative Disorders

Acute Myelofibrosis

Agnogenic Myeloid Metaplasia (myelofibrosis)

Polycythemia Vera

Essential Thrombocythemia

Lymphoproliferative Disorders

Non-Hodgkin's Lymphoma

Hodgkin's Disease

Phagocyte Disorders

Chediak-Higashi Syndrome

Chronic Granulomatous Disease

Neutrophil Actin Deficiency

Reticular Dysgenesis

Inherited Metabolic Disorders

Mucopolysaccharidoses (MPS)

Hurler's Syndrome (MPS-IH)

Scheie Syndrome (MPS-IS)

Hunter's Syndrome (MPS-II)

Sanfilippo Syndrome (MPS-III)

Morquio Syndrome (MPS-IV)

Maroteaux-Lamy Syndrome (MPS-VI)

Sly Syndrome, Beta-Glucuronidase Deficiency (MPS-VII)

Adrenoleukodystrophy

Mucolipidosis II (I-cell Disease)

Krabbe Disease

Gaucher's Disease

Niemann-Pick Disease

Wolman Disease

Metachromatic Leukodystrophy

Histiocytic Disorders

Familial Erythrophagocytic Lymphohistiocytosis

Histiocytosis-X

Hemophagocytosis

Inherited Erythrocyte Abnormalities

Beta Thalassemia Major

Sickle Cell Disease

Inherited Immune System Disorders

Ataxia-Telangiectasia

Kostmann Syndrome

Leukocyte Adhesion Deficiency

DiGeorge Syndrome

Bare Lymphocyte Syndrome

Omenn's Syndrome

Severe Combined Immunodeficiency (SCID)

SCID with Adenosine Deaminase Deficiency

Absence of T & B Cells SCID

Absence of T Cells, Normal B Cell SCID

Common Variable Immunodeficiency

Wiskott-Aldrich Syndrome

X-Linked Lymphoproliferative Disorder

Other Inherited Disorders

Lesch-Nyhan Syndrome

Cartilage-Hair Hypoplasia

Glanzmann Thrombasthenia

Osteopetrosis

Inherited Platelet Abnormalities

Amegakaryocytosis/Congenital Thrombocytopenia

Plasma Cell Disorders

Multiple Myeloma

Plasma Cell Leukemia

Waldenstrom's Macroglobulinemia

Other Malignancies

Breast Cancer

Ewing Sarcoma

Neuroblastoma

Renal Cell Carcinoma

Thus, the present invention may be used to treat a patient having a stem cell related disease by administration of a composition described herein, or by administering populations of stem cells produced by a method described herein.

The agonist is typically a phospholipid. The phospholipid may be a lysophospholipid and may have a sphingosine backbone. Preferably the agonist is selected from the group consisting of S1P, dihydro S1P, LPA, PAF and SPC or functional equivalents thereof. S1P and dihydro S1P are lysophospholipids with a sphingosine backbone, as is SPC, while LPA is a lysophosphopholipid with a glycerol backbone, and PAF is a phospholipid with a glycerol backbone.

The tyrosine kinase receptor may be PDGFR-α or PDGFR-β and the ligand a PDGF or functional equivalent thereof.

In a preferred embodiment the PDGF is PDGFaa, PDGFab or PDGFbb.

The method may also include use of TNF alpha, NGF (nerve growth factor), muscarinic acetylcholine agonists, serum or phorbol esters—which again are compounds that have additive or synergistic effects with S1P in other cell types.

Also provided is a pharmaceutical composition comprising a class III tyrosine kinase receptor ligand and a LPL receptor agonist. The composition may also include use of TNF alpha, NGF (nerve growth factor), muscarinic acetylcholine agonists, serum or phorbol esters—which again are compounds that have additive or synergistic effects with S1P in other cell types.

A skilled person will be able to provide formulations and dosage forms of the agonist. Furthermore, the optimum dosage for a given clinical situation could be determined by routine experimentation.

The compositions may be administered parenterally. For parenteral administration, the agonist and/or ligand may be combined with sterile aqueous or organic media to form injectable solutions or suspensions. The injectable solutions prepared in this manner may then be administered intravenously, intraperitoneally, subcutaneously, or intramuscularly. Additional methods of administration may include, but are not limited to, topical, sublingual, anal and vaginal methods of administration according to methods which are commonly known by those skilled in the art.

The amount of agonists or ligand used for preparation of a pharmaceutical composition should be varied according to principles well known in the art taking into account the severity of the condition being treated and the route of administration. In general, such a pharmaceutical composition would be administered to a warm blooded animal, preferably a mammal and most preferably a human, so that an effective dose, usually a daily dose administered in unitary or divided portions, is received. Dosages depend upon a number of factors, including the condition or disease being treated, characteristics of the subject and the type of pharmaceutical form or formulation used. Such deviations are within the scope of this invention.

Suitable pharmaceutically acceptable carriers for preparing a pharmaceutical composition include inert solid fillers or diluents and sterile aqueous or organic solutions. The antagonist and/or ligand are present in such pharmaceutical compositions in amounts sufficient to provide the desired dosage according to the range described above. Thus, for oral administration the agonist and/or ligand may be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. Controlled release, sustained release, and delayed release oral or parenteral compositions may be used.

The tablets, pills, capsules, and the like may also contain one or more binders such as gum tragacanth, acacia, corn starch or gelatin; one or more excipients such as dicalcium phosphate; one or more disintegrating agents such as corn starch, potato starch, alginic acid; one or more lubricants such as magnesium stearate; and a sweetening agent such as sucrose, lactose or saccharin. When a dosage unit form is a capsule, for example a gel capsule, it may contain, in addition to or instead of materials of the above type, a liquid carrier such as a fatty glyceride or mixtures of fatty glycerides. Dosage forms may also include oral suspensions.

Various other materials may be present as coatings or to modify the physical form of a dosage unit. For instance, tablets may be coated with shellac, sugar or both. A syrup or elixer may contain, in addition to the active ingredient(s), sucrose as a sweetening agent, methyl and propylparabens as preservatives, a dye and a flavoring such as cherry or orange flavor.

The pharmaceutical forms suitable for injectable use include sterile solutions or dispersions and sterile powders for the extemporaneous preparation of sterile injectable solutions or dispersions. In all cases, the form must be sufficiently fluid to enable incorporation into a syringe and injection therefrom and must be substantially stable under the conditions of manufacture and storage. In addition, the form must be substantially sterile and must be preserved against contamination of microorganisms such as bacteria and fungi. Sterilization may be achieved by filtration through microorganism retaining filters, by incorporating sterilizing agents into the compositions, or by irradiating or heating the compositions wherein such irradiation or heating is both appropriate and compatible with the applicable formulation.

Additional pharmaceutical forms may include suppositories, sublingual tablets, topical dosage forms and the like, and these may be prepared according to methods which are commonly known by those skilled in the art.

The present invention provides use of an agonist of the LPL receptors and a ligand of a class III tyrosine kinase receptor for modulating spontaneous differentiation of a stem cell having a lysophospholipid (LPL) receptor and PDGF receptors.

The present invention also provides use of a ligand of a class III tyrosine kinase receptor in modulating spontaneous differentiation of a stem cell.

The present invention further provides use of an agonist of the LPL receptor for modulating spontaneous differentiation of a stem cell having a lysophospholipid (LPL) receptor.

Preferably, the LPL receptor is selected from the group consisting of S1P1, S1P2 and S1P3.

Typically the agonist is a phospholipid.

The phospholipid or lysophoholipid may have a sphingosine backbone, and particularly, the lysophospholipid may be a phosphorlyated amino alcohol. Preferably the agonist is selected from the group consisting of S1P, dihydro S1P, LPA, PAF and SPC or functional equivalents thereof.

In a highly preferred form of the invention the lysophospholipid is sphingosine-1-phosphate (S1P) or a functional equivalent thereof.

Typically the ligand is a PDGF or functional equivalent thereof.

The tyrosine kinase receptor may be PDGFR-α or PDGFR-β.

In a preferred embodiment the PDGF is PDGFaa, PDGFab or PDGFbb which bind to the two types of receptors.

TNF alpha, NGF (nerve growth factor), muscarinic acetylcholine agonists, serum or phorbol esters may also be used as compounds that have additive or synergistic effects with S1P in other cell types.

The stem cell may be derived from foetal tissue or adult tissue.

The stem cell is typically an ES cell. Preferably the stem cell is a hES cell.

The present invention provides use of an agonist of the LPL receptor and a ligand of a class III tyrosine kinase receptor in producing a population of proliferating undifferentiated stem cells from a stem cell.

The present invention also provides use of a ligand of a class III tyrosine kinase receptor in producing a population of proliferating undifferentiated stem cells from a stem cell.

The present invention further provides use of a method of an agonist of the LPL receptor in producing a population of proliferating undifferentiated stem cells from a stem cell.

Preferably, the LPL receptor is selected from the group consisting of S1P1, S1P2 and S1P3.

Typically the agonist is a phospholipid.

Preferably the agonist is selected from the group consisting of S1P, dihydro S1P, LPA, PAF and SPC or functional equivalents thereof.

In a highly preferred form of the invention the lysophospholipid is sphingosine-1-phosphate (S1P) or a functional equivalent thereof.

Typically the ligand is a PDGF or functional equivalent thereof.

The tyrosine kinase receptor may be PDGFR-α or PDGFR-β.

In a preferred embodiment the PDGF is PDGFaa, PDGFab or PDGFbb which bind to the two types of receptors.

The ligand may also be TNF alpha, NGF (nerve growth factor), muscarinic acetylcholine agonists, serum or phorbol esters.

The stem cell may be derived from foetal tissue or adult tissue.

The stem cell is typically an ES cell. Preferably the stem cell is a hES cell.

Another aspect of the present invention is use of a composition containing an agonist of a LPL receptor and a ligand of a class III tyrosine kinase receptor in a method of treating or preventing a disorder of stem cell differentiation.

The present invention also provides use of a composition containing a ligand of a class III tyrosine kinase receptor in a method of treating or preventing a disorder of stem cell differentiation.

The agonist is typically a phospholipid. The phospholipid may be a lysophospholipid and may have a sphingosine backbone. Preferably the agonist is selected from the group consisting of S1P, dihydro S1P, LPA, PAF and SPC. S1P and dihydro S1P are lysophospholipids with a sphingosine backbone, as is SPC, while LPA is a lysophosphopholipid with a glycerol backbone, and PAF is a phospholipid with a glycerol backbone.

The tyrosine kinase receptor may be PDGFR-α or PDGFR-β and the ligand a PDGF or functional equivalent thereof.

In a preferred embodiment the PDGF is PDGFaa, PDGFab or PDGFbb.

The method may also include use of TNF alpha, NGF (nerve growth factor), muscarinic acetylcholine agonists, serum or phorbol esters—which again are compounds that have additive or synergistic effects with S1P in other cell types.

Abbreviations dH-S1P: dihydro-sphingosine-1-phosphate; EDG: endothelial differentiation gene; ERK: extracellular signal-regulated kinase; MAP kinase: mitogen-activated protein kinase; MEF: mouse embryonic fibroblasts; hES cells: human embryonic stem cells; LPA: lysophosphatidic acid; LPL: lysophospholipid; PAF: platelet-activated factor, PCNA: proliferating cell nuclear antigen; PDGF: platelet-derived growth factor, PDGFR: platelet-derived growth factor receptor; S1P: sphingosine-1-phosphate; SPC: sphingosylphosphorylcholine; SPK: sphingosine kinase.

BRIEF DESCRIPTION OF THE ACCOMPANYING FIGURES

FIG. 1: shows hES cells are target of S1P, LPA and PDGF. RT-PCR for LPL receptors (A, B), PDGFR-□ (alpha) and PDGFR-□ (beta) (C), SPK-1 and SPK-2 (D), with (+) or without (−) RT. Immunostaining of hES cells with Hoechst 33342 (E, H), PDGFR-□ (F) or PDGFR-□ (I) and GCTM-2 (G, J) antibodies. S1P, LPA and PDGF stimulate ERKs phosphorylation in hES cells. (K) Western blots experiment were performed using protein lysate from hES cells. Cells were pre-treated or not with U0126 (30 µM, 1 hr) and incubated for 5 min in the absence (C, control) or presence of S1P (S, 10 µM), LPA (L, 50 M) or PDGF (P, 20 ng/ml). The phosphorylation of Erk1 and Erk2 (P-Erk1 and P-Erk2) was assessed by immunoblotting with a polyclonal anti-active MAP kinase as described in Materials and Methods. After a stripping procedure, the same blots were reprobed with a monoclonal anti-MAP kinase, allowed the detection of Erk1 and Erk2. These data are representative of results from at least 3 independent experiments.

Figure 2:
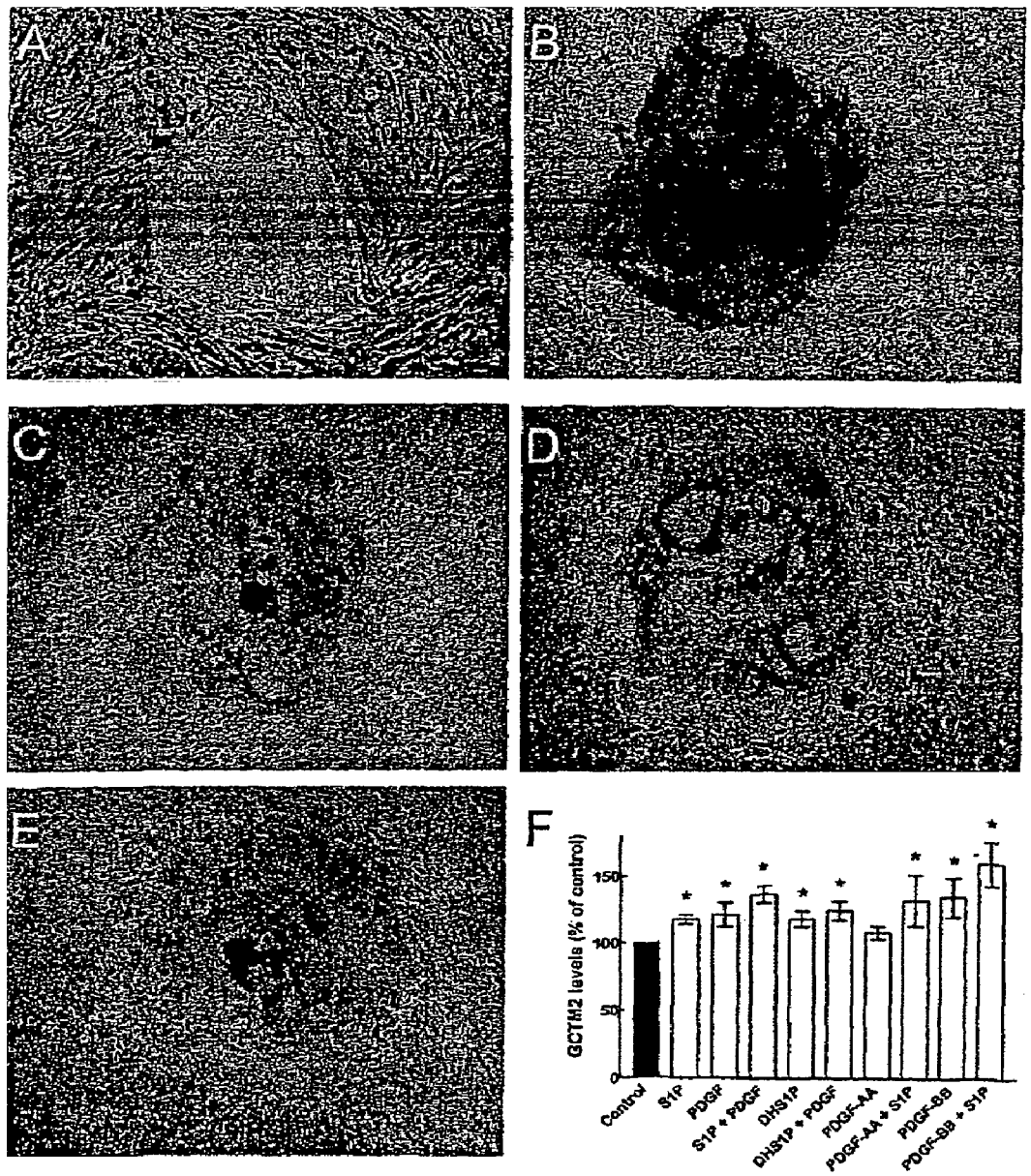

FIG. 2 shows S1P and PDGF inhibit the spontaneous differentiation of hES cells. (A) hES cells grown with MEF, before the depletion of serum from the medium. (B, C, D, E) hES cells grown without serum after 8 days, in the absence (B) or in the presence of S1P (10 µM) (C), PDGF (20 ng/ml) (D), S1P (10 µM) plus PDGF (20 ng/ml) (E). (F) hES cells grown without serum, in the presence or in the absence (control) of S1P (10 µM), PDGF (20 ng/ml), S1P (10 µM) plus PDGF (20 ng/ml). In A-E, data are representative of at least 3 independent experiments. In F, data expressed as percentages of alkaline phosphatase activity in absence of serum for eight days (% of control), are the means±SEM of at least 2 independent experiments, each run in triplicate.

Figure 3:
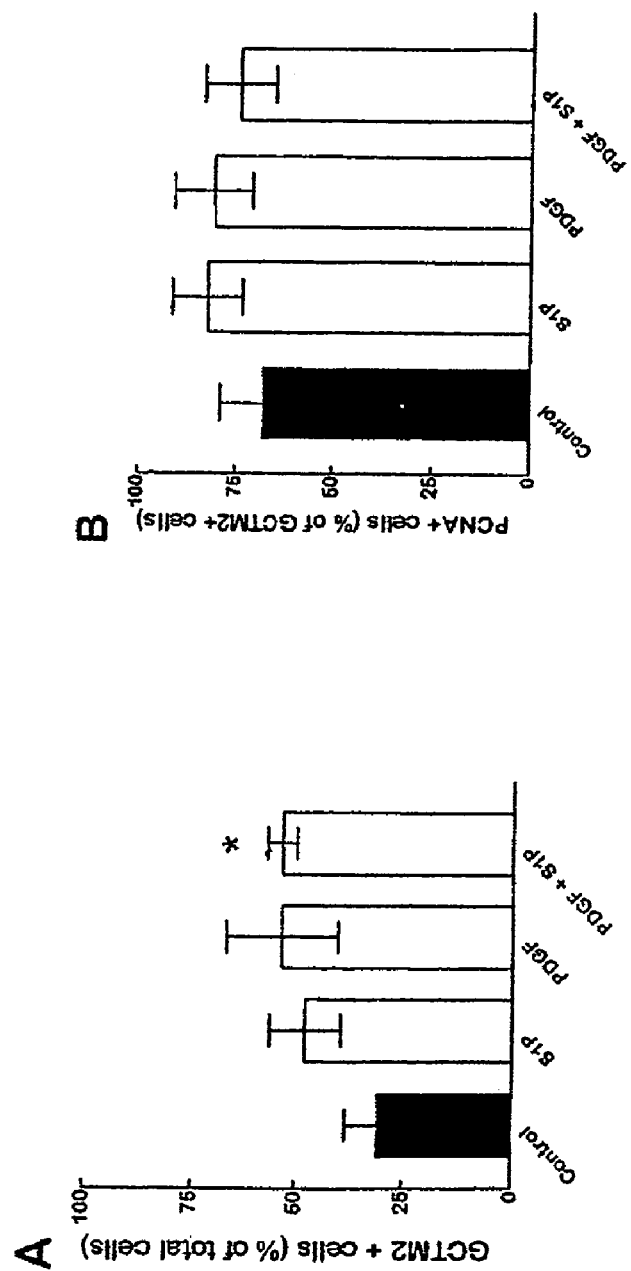

FIG. 3 shows S1P and PDGF inhibit the spontaneous differentiation of hES cells independently of MEF. hES cells mechanically dissociated and cultivated for 4 days in the absence (C, control) or presence of S1P (10 µM) or/and PDGF (20 ng/ml) in a media depleted in serum. (A) Quantification of the number of GCTM2+ cells. (B) Quantification of the number of PCNA+/GCTM2+ cells. These data are the mean±SEM of results obtained in at least 3 independent experiments.

Figure 4:
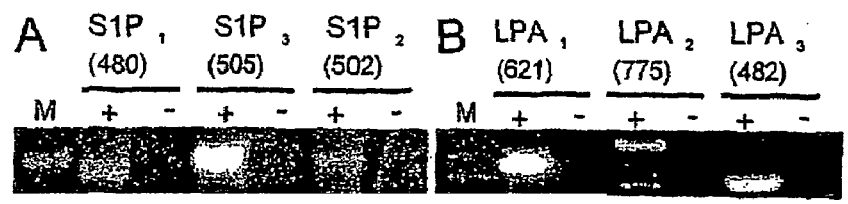
Figure 4:
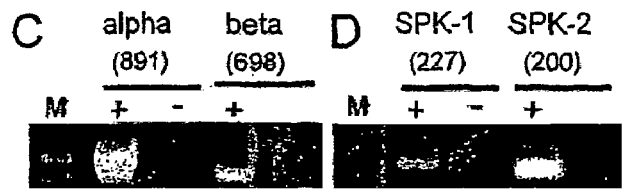
Figure 4:
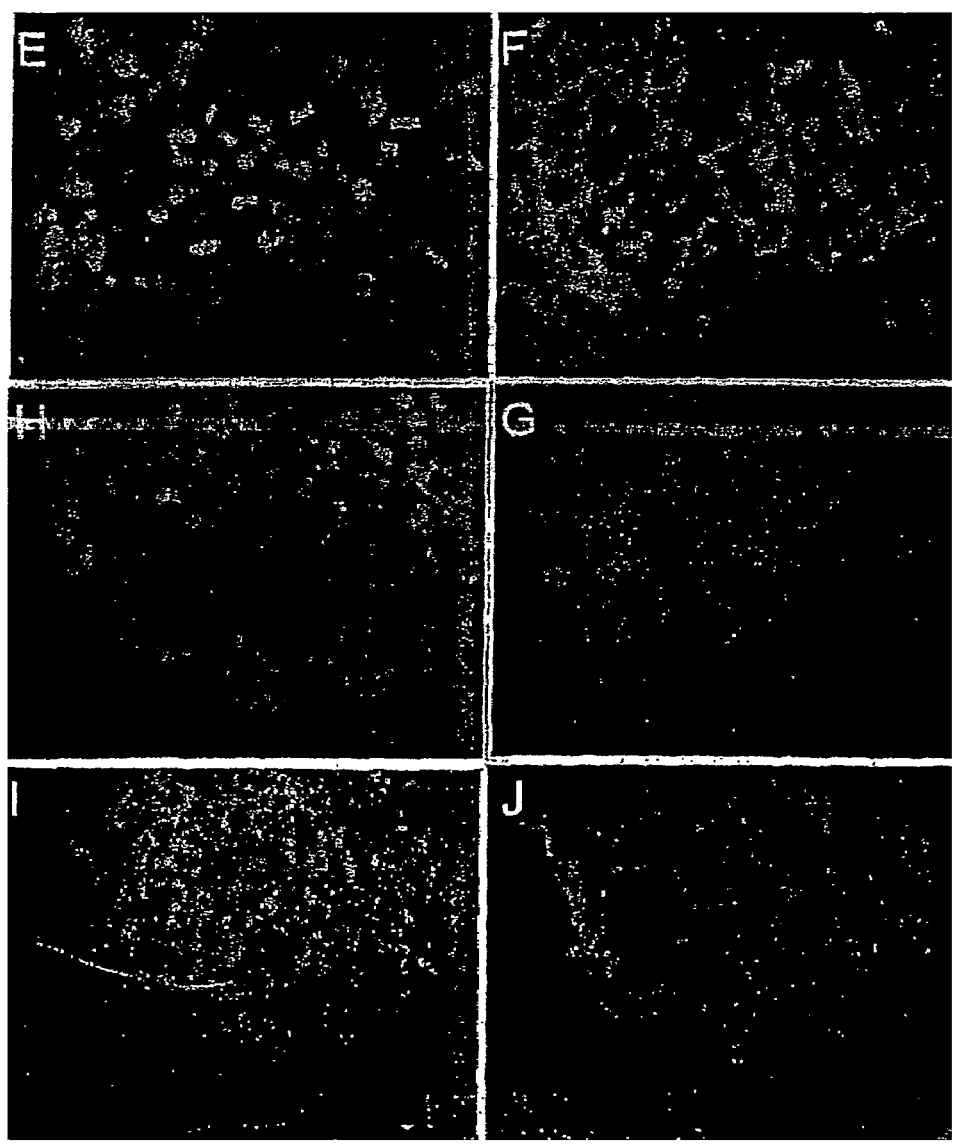

FIG. 4 shows hES cells are target of S1P, LPA and PDGF. RT-PCR for LPL receptors (A, B), PDGFR-□ (alpha) and PDGFR-□ (beta) (C), SPK-1 and SPK-2 (D), with (+) or without (−) RT. Immunostaining of hES cells with Hoechst 33342 (E, H), PDGFR-□ (F) or PDGFR-□ (I) and GCTM-2 (G, J) antibodies. S1P, LPA and PDGF stimulate ERKs phosphorylation in hES cells.

Figure 5:
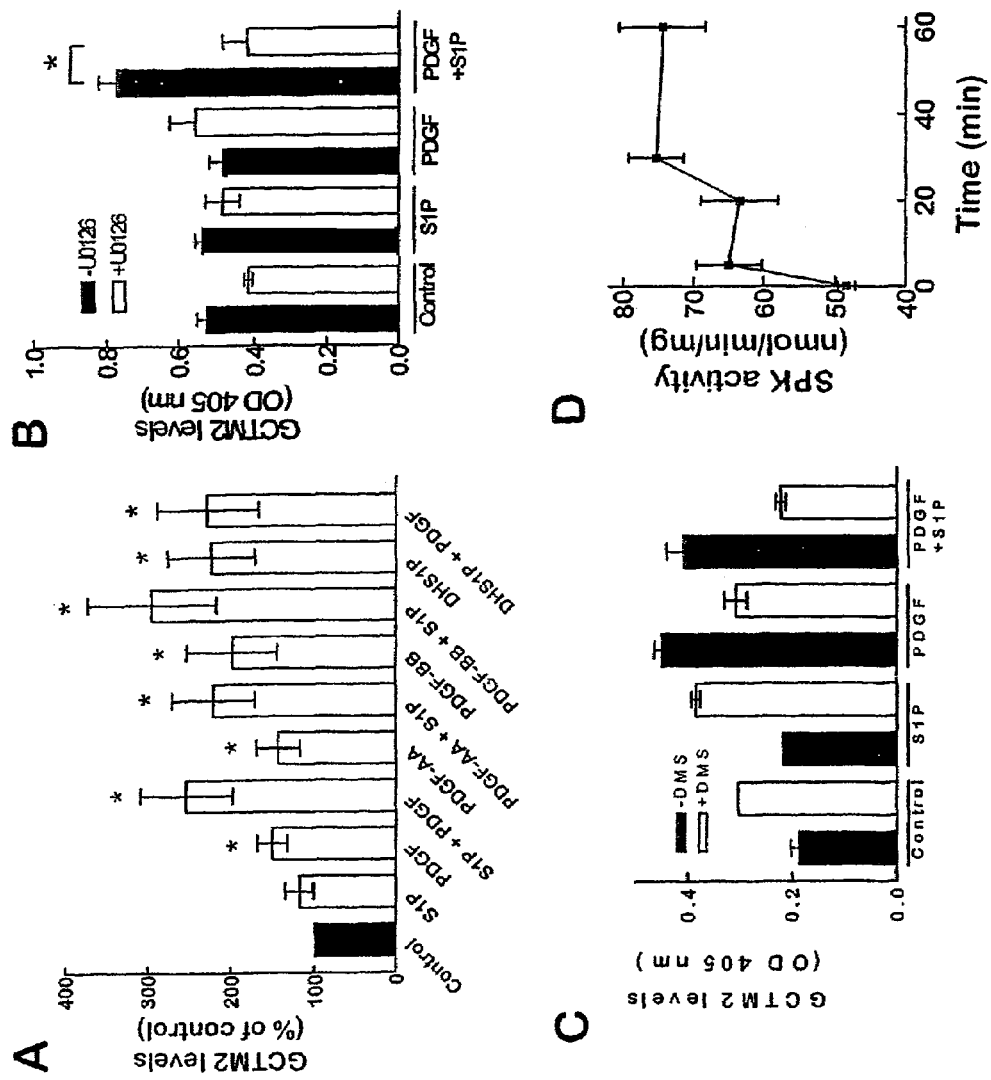

FIG. 5 shows S1P and PDGF inhibit the spontaneous differentiation of hES cells in the absence of serum. (A-C) hES cells with or without (control) the indicated agonists. Dihydro-S1P: DHS1P. (D) Sphingosine kinase activity measurement following incubation of hES cells with PDGF.

Figure 6:
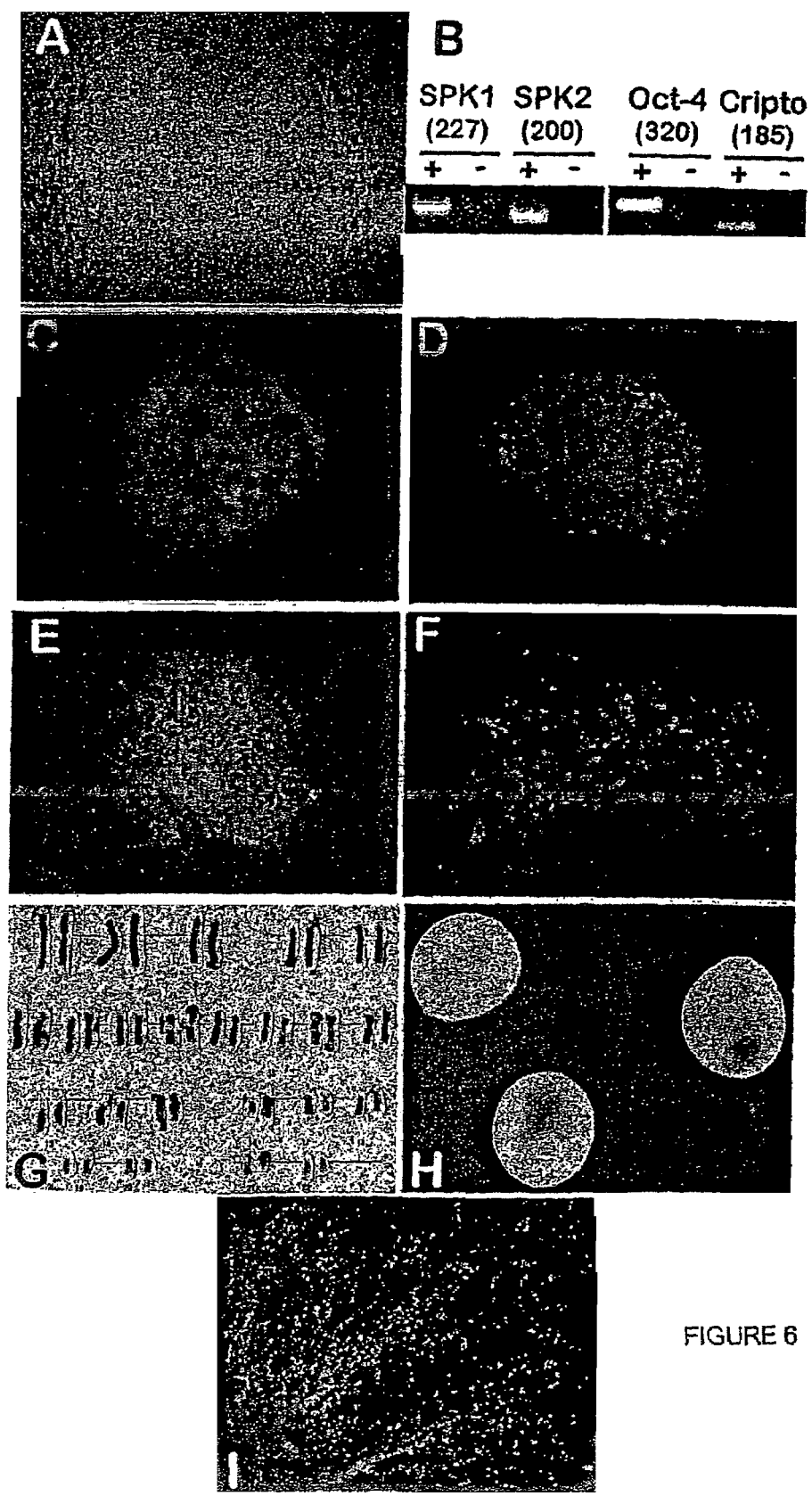
Figure 7:
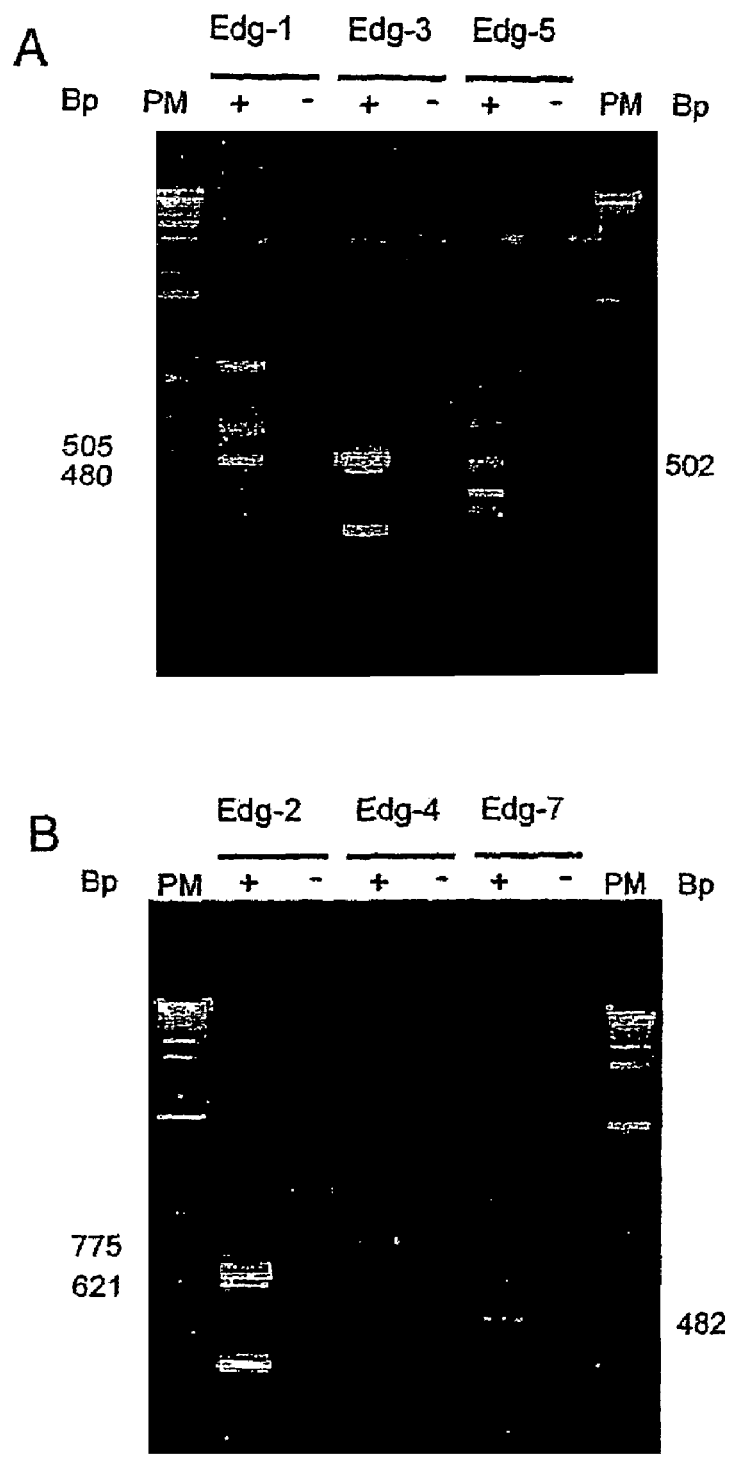

FIG. 6 shows characterization of hES cells. (A) hES cells grown in the presence of S1P+PDGF, passage 14. (B) RT-PCR using mRNA from hES cells grown in the presence of S1P and PDGF using specific primers for Oct-4, cripto, SPK1 and SPK2, with (+) or without (−) RT, passage 7. Immunostaining of hES cells grown in the presence of S1P+PDGF with GCTM-2 (C), Oct-4 (D), TG-30 (E) or TRA-1-60 (F), passage 13. (G) Karyotyping of hES cells grown in the presence of S1P+PDGF, passage 8. (H) Neuronal differentiation into neurospheres. (I) βtubulin immunostaining FIG. 7 shows Edg receptor mRNAs are expressed in hES cells. RT-PCR experiments were performed using mRNA isolated from hES cells using specific primers for human Edg receptors. In each case, experiments were conducted either in the presence (+) or absence (−) of reverse transcriptase. The RT-PCR products were separated by electrophoresis on 1.5% agarose gel and revealed by ethidium bromide fluorescence. Molecular sizes (in bp) of the products were calculated using 1 kB plus DNA ladder markers (M). These data are representative of at least 6 independent experiments, each carried out on mRNAs prepared from different cultures of hES cells.

Figure 8:
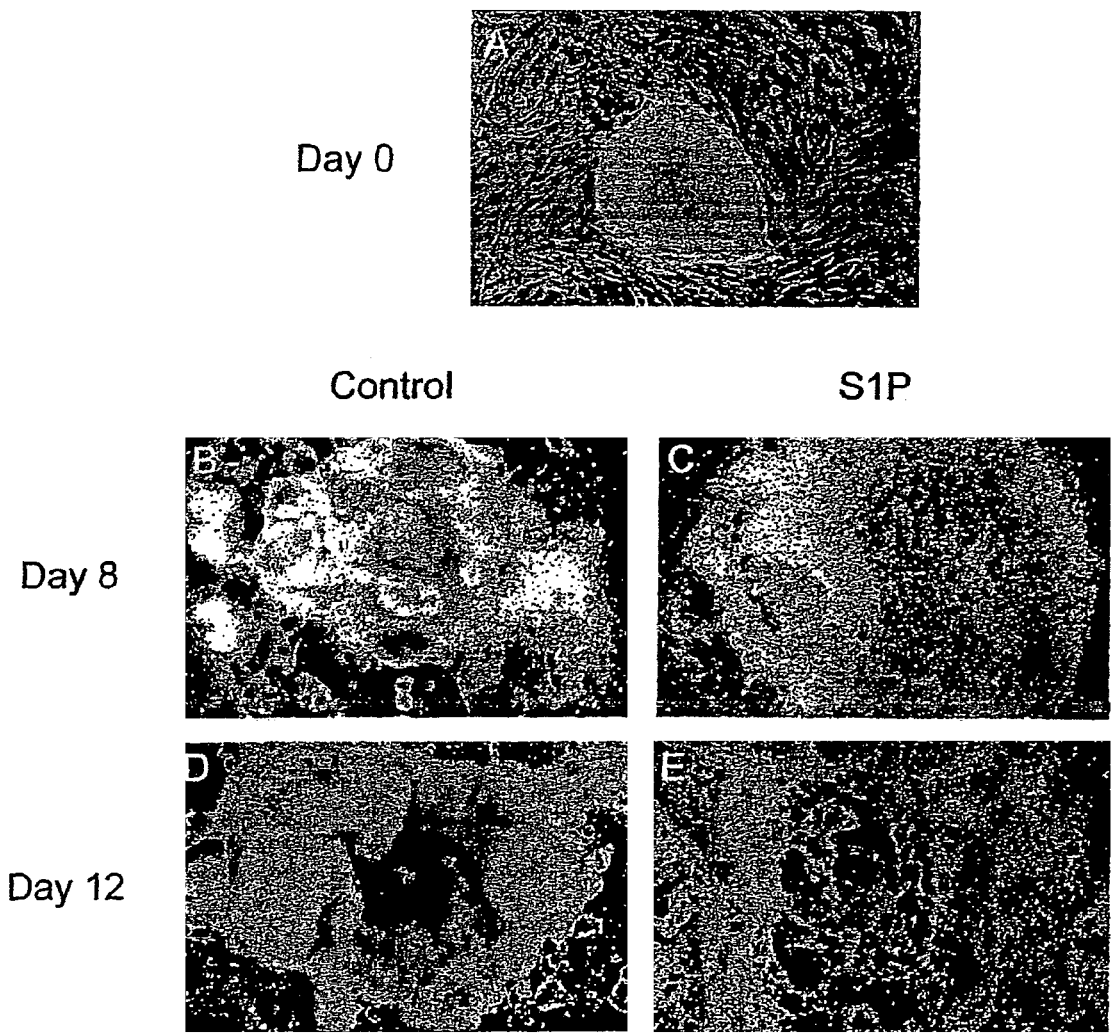

FIG. 8 shows S1P inhibits the spontaneous differentiation of hES cells. (A) hES cells grown with feeder, before the depletion in serum. (B) hES cells grown without serum after 8 days (B, C) and 12 days (D, E), in absence (B, D) or presence of S1P (C, E, 10 µM). These data are representative of at least 3 independent experiments.

Figure 9:
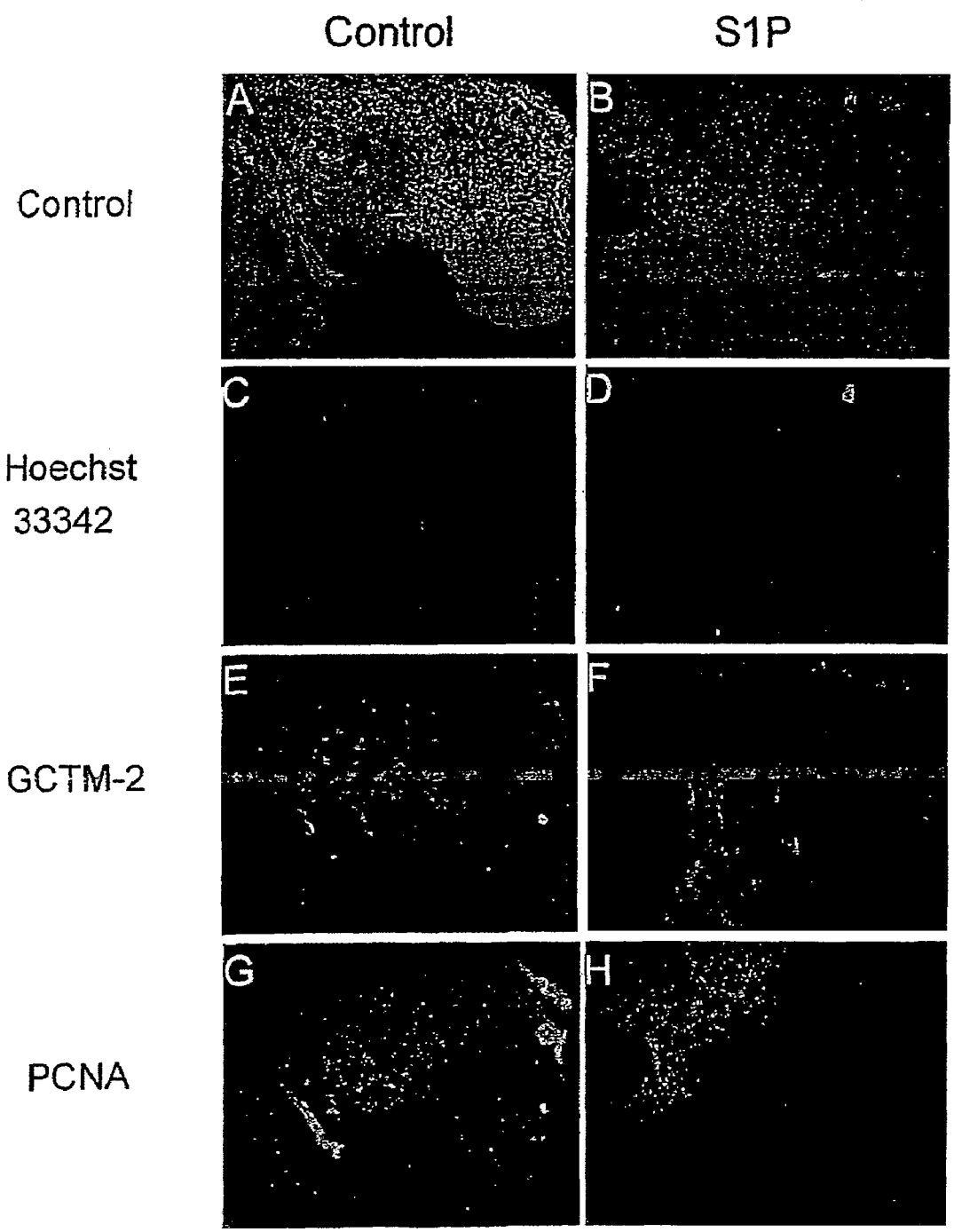

FIG. 9 shows S1P inhibits the spontaneous differentiation of hES cells. Double staining experiments were performed using antibodies for PCNA and GCTM-2. These data are representative of at least 3 independent experiments.

Figure 10:
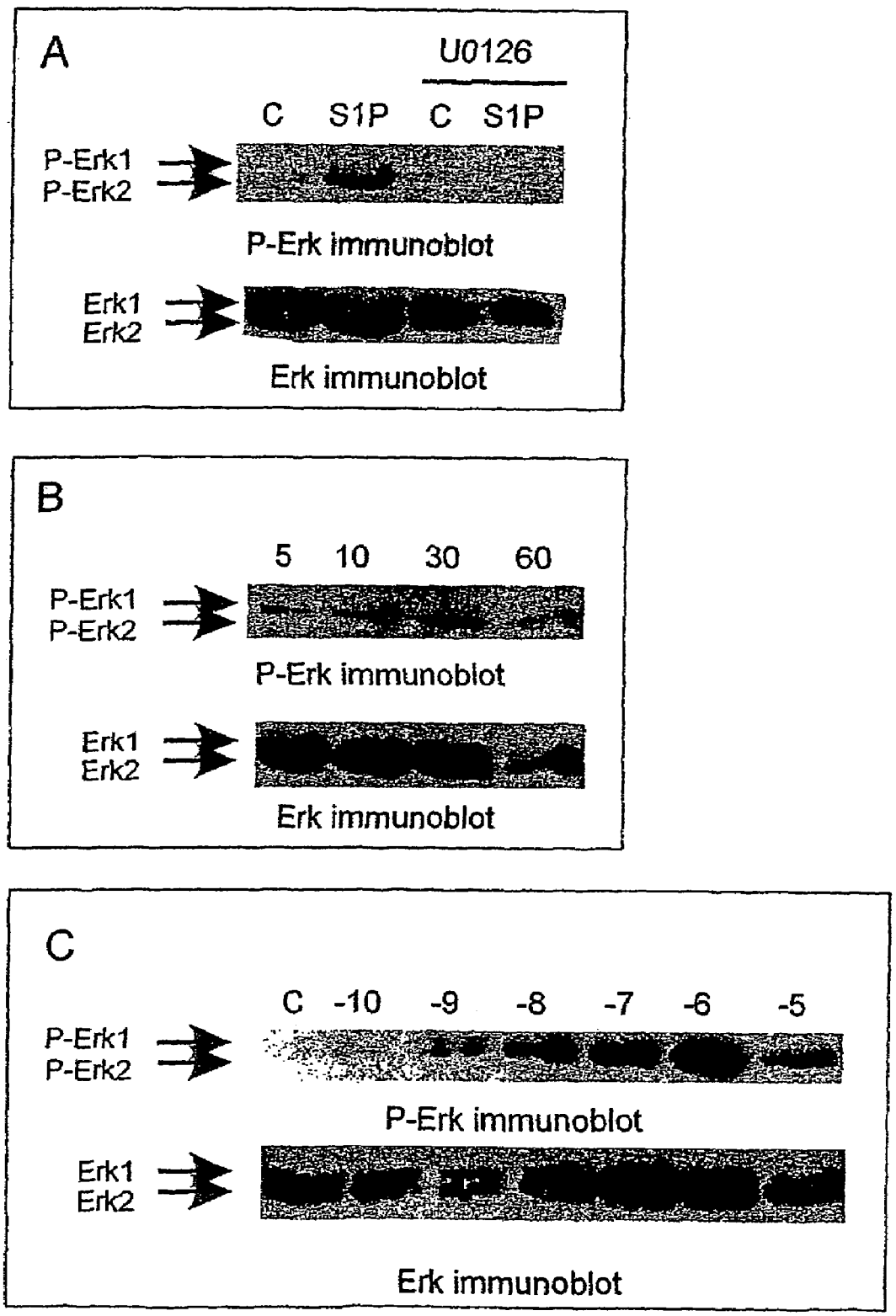

FIG. 10 shows S1P stimulates ERKs phosphorylation in hES cells. Western blots experiments were performed using protein lysate from hES cells. (A) Cells were pre-treated or not with U0126 (30 µM, 1 hr) and incubated for 5 min in the absence (C, control) or presence of S1P (10 µM). (B) Cells were incubated for different time periods in the absence or presence of S1P (10 µM). (C) Cells were incubated for 5 min with various concentrations of S1P. The phosphorylation of Erk1 and Erk2 (P-Erk1 and P-Erk2) was assessed by immunoblotting with a polyclonal anti-active MAP kinase as described in Materials and Methods. After a stripping procedure, the same blots reprobed with a monoclonal anti-MAP kinase, allowed the detection of Erk1 and Erk2. These data are representative of at least 3 independent experiments.

Figure 11:
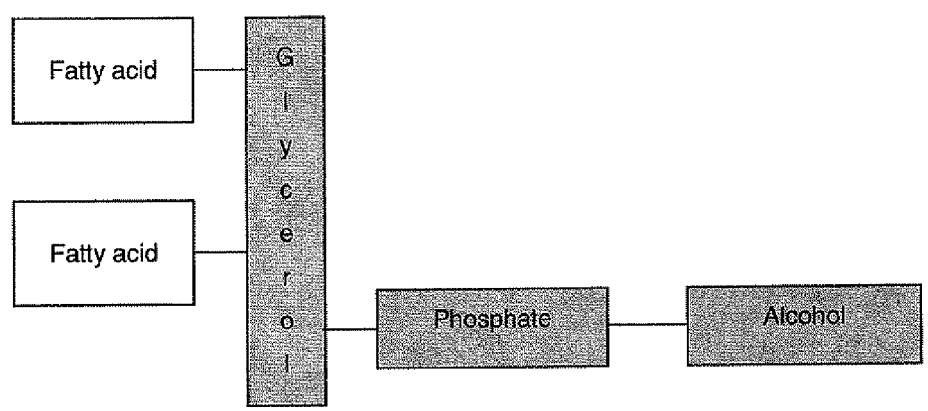

FIG. 11 provides a diagram of a generic phospholipid.

The invention will now be more fully described with reference to the following non-limiting Examples.

BEST METHOD AND OTHER METHODS OF CARRYING OUT THE PRESENT INVENTION

Example 1

Cell Culture hES-3 cells were cultured as previously described[1]. The serum-free culture medium consisted of DMEM (without sodium pyruvate, glucose 4500 mg/l, Invitrogen, Mount Waverley, VIC, Australia) supplemented with insulin/transferrin/selenium 1%, β-mercaptoethanol 0.1 mM, NEAA 1%, glutamine 2 mM, Hepes 25 mM, penicillin 50 U/ml and streptomycin 50 mg/ml (all from Invitrogen). Medium was changed every 2 days and cells were passaged every week. S1P and dihydro-S1P were obtained from Biomol (Plymouth Meeting, Pa., USA) and were dissolved in methanol. LPA was obtained from Sigma (Castle Hill, NSW, Australia) and was dissolved in ethanol. Extemporaneous dilutions of all lipids were made in water containing 0.1% fatty acid-free bovine serum albumin (BSA) (Sigma). Human PDGF-AB, PDGF-AA, PDGF-BB were from PreproTech Inc. (Rocky Hill, N.J., USA).

RT-PCR Experiments

Total RNA was extracted from hES cells and reverse transcribed (RT) as previously described[1]. The cDNA samples were amplified by PCR with sense and antisense primers (Sigma) designed for the specific detection of mouse (data not shown) or human DNA target sequences (Table 1) using Taq DNA polymerase (Biotech International Ltd, Perth, Wash., Australia) as previously described[18]. The specific amplified DNA fragments were sized by electrophoresis on 1.5% (w/v) agarose gel and stained with ethidium. Molecular sizes (bp) were calculated using 1 kb plus DNA ladder markers (M). The amplicons were purified and sequenced. Experiments were performed on hES-2 and hES-3.

TABLE 1

Sense and antisense primers

| Gene | sense and antisense primers | Size (bp) | Annealing temp (° C.) | References |
|---|---|---|---|---|
| $SiP_1$ | CCACAACGGGAGCAATAACT | 480 | 52 | [2](SEQ ID NO:1) |
|  | GTAAATGATGGGGTTGGTGC |  |  | (SEQ ID NO:2) |
| $SiP_2$ | CCAATACCTTGGTCTCTCTGGC | 502 | 52 | [2](SEQ ID NO:3) |
|  | CAGAAGGAGGATGCTGAAGG |  |  | (SEQ ID NO:4) |
| $SiP_3$ | TCAGGGAGGGCAGTATGTTC | 505 | 52 | [2](SEQ ID NO:5) |
|  | CTGAGCCTTGAAGAGGATGG |  |  | (SEQ ID NO:6) |
| $SiP_4$ | CGGCTCATTGTTCTGCACTA | 701 | 52 | [2](SEQ ID NO:7) |
|  | GATCATCAGCACCGTCTTCA |  |  | (SEQ ID NO:8) |
| $SiP_5$ | TTCTGATACCAGAGTCCGGG | 460 | 52 | [2](SEQ ID NO:9) |
|  | CAAGGCCTACGTGCTCTTCT |  |  | (SEQ ID NO:10) |
| $LPA_1$ | GCTCCACACACGGATGAGCAACC | 621 | 56 | [3](SEQ ID NO:11) |
|  | GTGGTCATTGCTGTGAACTCCAGC |  |  | (SEQ ID NO:12) |
| $LPA_2$ | AGCTGCACAGCCGCCTGCCCCGT | 775 | 56 | [3](SEQ ID NO:13) |
|  | TGCTGTGCCATGCCAGACCTTGTC |  |  | (SEQ ID NO:14) |
| $LPA_3$ | CCATAGCAACCTGACCAAAAAGAG | 482 | 56 | [3](SEQ ID NO:15) |
|  | TCCTTGTAGGAGTAGATGATGGGG |  |  | (SEQ ID NO:16) |
| PDGFRα | ATCAATCAGGCCAGATGGAC | 891 | 58 | [4](SEQ ID NO:17) |
|  | TTCACGGGCAGAAAGGTACT |  |  | (SEQ ID NO:18) |
| PDGFRβ | AATGTCTCCAGCACCTTCGT | 698 | 58 | [4](SEQ ID NO:19) |
|  | AGCGGATGTGGTAAGGCATA |  |  | (SEQ ID NO:20) |
| Crypto | CAGAACCTGCTGCCTGAATG | 185 | 55 | (SEQ ID NO:21) |
|  | GTAGAAATGCCTGAGGAAACG |  |  | (SEQ ID NO:22) |
| SPK-1 | ACCCATGAACCTGCTGTCTCT | 227 | 55 | (SEQ ID NO:23) |
|  | CAGGTGTCTTGGAACCCACT |  |  | (SEQ ID NO:24) |
| SPK-2 | TGGCAGTGGTGTAAGAACC | 200 | 55 | (SEQ ID NO:25) |
|  | CAGTCAGGGCGATCTAGGA |  |  | (SEQ ID NO:26) |
| Oct-4 | CGTTCTCTTTGGAAAGGTGTTC | 320 | 55 | [5](SEQ ID NO:27) |
|  | ACACTCGGACCACGTCTTTC |  |  | (SEQ ID NO:28) |

Immunofluorescence.

In some experiments, hES-3 cells plated onto 8-well chamber slides, with or without MEF, were fixed in ethanol or paraformaldehyde (for PDGFR) the day after plating. In others, hES-3 cells were mechanically dissociated, in order to obtain a monolayer culture and then plated onto 8-well chamber slides without MEF and were fixed in ethanol 4 days after the first treatment. Immunostaining was performed using the following antibodies: anti human PDGFR-α or PDGFR-β (R&D Systems Inc.), GCTM-2, and/or PCNA (Chemicon, Boronia, VIC, Australia), TRA-1-60, Oct-4. Nuclei were evidenced by Hoechst-33342. Slides were mounted and observed by fluorescent microscopy with a Leica microscope at ×10, ×20 and ×40. Specificity was verified by the absence of any staining in the negative controls. In some experiments, cells were counted to determine the ratio of GCTM-2 positive (GCTM2+), PCNA positive (PCNA+) and GCTM2+/PCNA+ cells within the global population.

GCTM-2 Quantification.

hES-3 cells plated with MEF, were fixed in ethanol and immunostained with GCTM-2 and then with an alkaline phosphatase-coupled secondary antibody (Dako). The activity of alkaline phosphatase was detected by adding a solution of 4-nitrophenyl phosphate (Roche, Mannheim, Germany), followed by reading the optical density (OD) at 405 nm. In order to validate the technique as a relevant indicator of the proportion of GCTM-2 positive cells, standard curves were done with the teratocarcinoma cell line GCT27C4, known to express GCTM-2. This showed a linear correlation between the number of cells and the OD read at 405 nm (data not shown).

Western Blot Analysis.

hES-3 cells plated without MEF for 24 hrs were depleted of serum for a further 18 hrs. Cells pre-treated or not with U0126 (Sigma, 30 µM, 1 hr), were incubated in the presence of the different agents for 5 min and were lysed by removal of the supernatants and addition of a reducing loading buffer containing 1 mM sodium orthovanadate (Sigma). Protein lysates (approx. 80 µg) were separated by SDS-polyacrylamide gel electrophoresis (10% polyacrylamide, w/v), transferred to nitrocellulose (Hybond-nitrocellulose, Amersham) and immunoblotting was carried out using rabbit polyclonal anti-active mitogen-activated protein (MAPK) antibodies raised against a dually phosphorylated MAPK peptide (Promega, Madison, Wis., USA). Peroxidase-coupled secondary antibody (Dako) was detected by exposure of autoradiographic films in the presence of a chemiluminescent detection reagent (ECL, Amersham). Stripping of antibodies was achieved and membranes were then reprobed with rabbit polyclonal anti-ERK1/2 antibodies (Promega), and then with peroxidase-coupled secondary antibodies (Dako). Membranes probed with either rabbit polyclonal anti-active p38 (Promega) or rabbit polyclonal anti-active JNK (Promega) antibodies were also performed, using the same procedure as described above.

Protein Quantification.

hES-3 cells were lysed and the amount of proteins was determined using a colorimetric assay based on the Bradford dye-binding test (Bio-Rad Laboratories, Regents Park, NSW, Australia).

Statistical Analysis.

Each set of experiments was performed at least 3 times (n refers to number of independent experiments performed on different cell cultures). Data are expressed as the mean±SEM. Significance of the differences was evaluated by using the ANOVA followed by Student-Newman Keuls test. Values of $P<0.05$ were considered significant and were respectively indicated by *.

Results hES cells (FIG. 1A) expressed mRNA transcripts for three S1P receptors: $S1P_1$, $S1P_2$ and $S1P_3$ and for each of LPA receptors: $LPA_1$, $LPA_2$ and $LPA_3$ (FIG. 1B), while these cells did not express mRNA for $S1P_4$ and $S1P_5$ (data not shown). hES cells also expressed mRNA transcripts for PDGFR-α (FIG. 1C) and PDGFR-β (FIG. 1C) as well as the corresponding proteins, as revealed by immunostaining (FIG. 1E-J). MEF expressed $S1P_1$, $S1P_2$, $S1P_3$, $LPA_1$ and $LPA_2$, PDGFR-α and PDGFR-β but neither $S1P_4$, $S1P_5$ nor $LPA_3$ (data not shown), as previously shown by others[6-8]. Because the MAP kinases ERKs are implicated in cell proliferation and differentiation, we examined the effects of S1P, LPA and PDGF-AB (PDGF) on their activation in hES cells. After 5 min, S1P, LPA and PDGF stimulated the phosphorylation of ERKs in hES cells (FIG. 1K), an effect that was totally inhibited in presence of the MEK inhibitor U0126 (30 µM) (FIG. 1K).

Next, it was examined whether S1P, LPA and PDGF could modulate the fate of hES cells. When hES cells were grown on MEF, in a serum-free culture media, they spontaneously differentiated. As shown in FIG. 2, after 8 days in such conditions (control), the colonies were bigger than those observed before the removal of serum (FIG. 2A) and hES cells gave rise to different kinds of cells (FIG. 2B). After 8 days, LPA (up to 50 µM) did not have an obvious effect on growth of the colonies, as ascertained by morphological (data not shown) whilst in the presence of either S1P (10 µM) or PDGF (20 ng/ml), the colonies appeared flatter and less differentiated as compared to the control condition (FIGS. 2C, 2D). Thus, after 8 days of treatment, when GCTM-2 levels of cells were quantified by measuring the activity of alkaline phosphatase, cells treated with S1P or PDGF were respectively 16.6±4.1% (n=7) and 16.6±7.0% (n=7) more GCMT2+ than the control cells (FIG. 2F). Strikingly, the co-incubation of both S1P (10 µM) and PDGF (20 ng/ml) induced a strong inhibition of spontaneous differentiation, not observed in the presence of one or the other agent (FIG. 2E) with a higher percentage of GCTM2+ cells of 40.1±7.5% (n=7) than in the control cells (FIG. 2F). As GCTM-2 is a stem cell marker, these results suggest that the combination of PDGF and S1P in a serum-free culture media strongly prevents the spontaneous differentiation of hES cells.

In order to identify the effects of S1P and PDGF on hES cells, we carried out experiments in which we forced the cells to differentiate, by 1) mechanically dissociating them before plating and 2) growing them in the absence of MEF and serum. S1P or/and PDGF were added to the culture medium and their effects on differentiation and proliferation were quantified by immunostaining the cells with PCNA, a marker of proliferation, and GCTM-2 (FIG. 3). After 4 days in medium without serum, most of the control cells were differentiated, with only 30.8±7.7% (n=13) of GCTM2+ cells (FIG. 3A). By contrast, when either S1P (10 µM) or PDGF (10 ng/ml) was added to the medium, 47.9±3.8% (n=13) or 53.7±13.2% (n=3) of the cells respectively were GCTM2+, and 53.7±3.5% (n=3) of the cells were GCTM2+ in presence of both S1P and PDGF. Within the hES cell population, a large proportion expressed PCNA, showing that the majority of these stem cells still proliferated (FIG. 3B). However, there was no statistically significant difference in the proliferating rate of hES cells between the control cells and the ones treated with either S1P or/and PDGF (FIG. 3B). Altogether, these data suggest that S1P and PDGF mostly act on the differentiation of hES cells grown in the absence of serum rather then on the proliferating state of hES cells. Moreover, because the hES cells were cultivated in absence of MEF, these experiments clearly show that S1P and PDGF are able to directly target the hES cells.

We next investigated the effect of dihydrosphingosine-1-phosphate (dihydro-S1P, 10 µM), an S1P analogue that can only mimics the receptor-dependent effects of S1P. By measuring the GCTM2 levels of the cells, we showed that the effect seen in presence of S1P and PDGF was mimicked by dihydro-S1P and PDGF (125.7±9.7% of control (n=3)), demonstrating that S1P's effect is receptor-dependent (FIG. 2F). We then investigated which isoform of PDGF was the most potent in inhibiting the spontaneous differentiation of hES cells. When added with S1P, the isoform BB was the most potent (182.0±26.0% of control (n=2)), followed by AB (125.7±9.7% of control (n=3)), while AA elicited little effect (120.5±4.5% of control (n=2)) (FIG. 2F).

Passaging

The hES cells have successfully been passaged through at least 18 passages in PDGF and S1P, with no serum. After passage 13 the cells have stained positive for the stem cell markers GCTM-2, Oct-4 and TG30. After passage 7 the cells expressed mRNA for SPK1 and SPK2 showing the probable expression of the enzymes as well as the stem cell markers Oct-4, and Crypto. After passage 8: karyotyping of hES cells—is being carried out to show that these cells when cultured in serum free conditions with PDGF and S1P have maintained a normal karyotype.

Discussion

Since hES cells spontaneously differentiate in culture, a phenomenon that leads to a loss of their pluripotency, the identification of the compounds that are able to prevent this differentiation is of particular interest. In this study, we describe for the first time that hES cells are targets of S1P, LPA and PDGF.

As revealed by RT-PCR analysis, these cells express the mRNA for the receptors $S1P_1$, $S1P_2$, $S1P_3$, $LPA_1$, $LPA_2$ and $LPA_3$. Referring to studies performed in rodent or in human, these receptors are widely expressed in the body (for reviews see[9,10]). The absence of expression of $S1P_4$ and $S1P_5$ in these cells is in accordance with the fact that these receptors seem to be mostly expressed in highly differentiated tissues, such as lymphoid tissue for $S1P_4$[11] and in brain's white matter for $S1P_5$[12]. Moreover, hES cells express the PDGF-receptors α and β, as revealed by RT-PCR and immunostaining. In hES cells, the addition of both PDGF and S1P inhibit very strongly the spontaneous differentiation, suggesting that these two molecules do cross talk. These combined effects could be attributed to the fact that 1) PDGF stimulates the formation of intracellular S1P which would then act as a second messenger, for instance in the regulation of calcium homeostasis[13] and in the suppression of apoptosis, as shown in fibroblasts[14] and other cell types[15,16], but up to now the intracellular targets of S1P remain unclear; 2) S1P acts extracellularly through its receptors, and thus activates different intracellular signalling pathways, such as the MAP kinases, involved in cell proliferation. The presence of both intracellular and extracellular S1P might then lead to a stronger inhibition of differentiation than the ones observed in presence of either S1P or PDGF. Also reported is a new cross link between PDGF and S1P signals, in which both molecules need to be present. Such a mechanism has recently been described for the first time by Katsuma et al. (2002)[17] in mesangial cells.

As shown by others, S1P, LPA and PDGF receptors are expressed in MEF[7] and these molecules are able to regulate multiple signalling pathways. Thus, Ishii et al. (2001) demonstrated that in these cells, S1P activates phospholipase C, inhibits the production of cAMP and activates Rho[7]. In MEF, PDGF stimulates migration. The effect observed in presence of PDGF and S1P on hES cells might be in part due to an effect through the MEF.

S1P, LPA and PDGF are all present in serum from different species, including bovine and human. However, the concentration of these molecules varies from one species to another. Thus, it is believed that this could explain the commonly observed phenomenon with current cell culturing techniques where there is not only species dependant variation in the performance of serum used to supplement cell culture systems but also intra-species batch to batch variations as well.

Altogether, these data suggest that within the lipids and the proteins present into the serum, both S1P and PDGF are key elements in the regulation of spontaneous differentiation of hES cells. Identification of compounds having an ability to inhibit differentiation allows the design of simple culture media more suitable for hES cell propagation. Moreover, in a therapeutic view, it is important to determine compounds that allow cultivation of hES cells in a serum-free environment.

Example 2

Cell Culture hES-3 cells were cultured as previously described[1]. The serum-free culture medium consisted of DMEM (without sodium pyruvate, glucose 4500 mg/l, Invitrogen, Mount Waverley, VIC, Australia) supplemented with insulin/transferrin/selenium 1%, β-mercaptoethanol 0.1 mM, NEAA 1%, glutamine 2 mM, Hepes 25 mM, penicillin 50 U/ml and streptomycin 50 mg/ml (all from Invitrogen). Media was changed every 2 days and cells were passaged every week S1P and dihydro-S1P were obtained from Biomol (Plymouth Meeting, Pa., USA). LPA was obtained from Sigma (Castle Hill, NSW, Australia). Extemporaneous dilutions of all lipids were made in water containing 0.1% fatty acid-free bovine serum albumin (BSA) (Sigma). S1P and dihydro-S1P were used at 10 mM. Human PDGF-AB, PDGF-AA, PDGF-BB were from Prepro Tech Inc. (Rocky Hill, N.J., USA) and were used at 20 ng/ml.

RT-PCR Experiments.

Total RNA was extracted from hES cells and reverse transcribed (RT) as previously described[1]. The cDNA samples were amplified by PCR with sense and antisense primers (Sigma) designed for the specific detection of mouse (data not shown) or human DNA target sequences (Table 1) using Taq DNA polymerase (Biotech International Ltd, Perth, WA, Australia) as previously described[18]. The specific amplified DNA fragments were sized by electrophoresis on 1.5% (w/v) agarose gel and stained with ethidium. Molecular sizes (bp) were calculated using 1 kb plus DNA ladder markers (M). The amplicons were purified and sequenced. Experiments were performed on hES-2 and hES-3.

Immunofluorescence.

Cells were fixed in paraformaldehyde 4% (for PDGFR staining) or 100% ethanol and immunostained as previously described[1] using the following antibodies: anti-human PDGFR-α or PDGFR-β (R&D Systems Inc., Minneapolis, Minn., USA), GCTM-2 (this laboratory), TRA-1-60 (gift from P. Andrews, University of Sheffield), Oct-4 (Santa Cruz, Calif., USA), TG-30 (this laboratory). Nuclei were counterstained with Hoechst-33342 (Chemicon). Specificity was verified by the absence of any staining in the negative controls.

Sphingosine Kinase Activity.

hES-3 cells plated without MEF for 24 hr and depleted of serum for a further 18 hr were incubated in the presence of PDGF (20 ng/ml) for various time periods and were harvested and lysed by sonication (2 W for 30 s at 4° C.) in lysis buffer containing 50 mM Tris/HCl (pH 7.4), 10% glycerol, 0.05% Triton X-100, 150 mM NaCl, 1 mM dithiothreitol, 2 mM $Na_3VO_4$, 10 mM NaF, 1 mM EDTA and protease inhibitors (Complete™, Roche, Mannheim, Germany). SPK activity was determined using D-erythro-sphingosine and $[\alpha^{32}P]ATP$ as substrates, as previously described[19]. Protein concentrations in cell homogenates were determined with Coomassie Brilliant Blue reagent (Bio-Rad, Regent Park, NSW, Australia) using bovine serum albumin as standard.

GCTM-2 Quantification.

Cells were fixed in 100% ethanol and immunostained with GCTM-2 followed by alkaline phosphatase-coupled secondary antibodies (Dako). Alkaline phosphatase activity was detected by adding a solution of 4-nitrophenyl phosphate (Roche), and the concentration of the reaction product was determined by reading the optical density (OD) at 405 nm. In order to validate the technique as an accurate indicator of the proportion of GCTM-2 positive cells, standard curves were carried out with the embryonal carcinoma cell line GCT27C4, known to express GCTM-2[20]. This showed a linear correlation between the number of cells and the OD read at 405 nm (data not shown).

Neuronal Induction of hES Cells.

hES-3 cells (passages 11, 13-15) were differentiated into noggin cells by a noggin treatment then into neurospheres and last into neurons as previously described in PCT/AU01/00735.

Statistical Analysis.

All experiments were performed at least 3 times. Data are expressed as the mean±SEM of at least 3 independent experiments. Significance of the differences was evaluated using an ANOVA followed by Student-Newman Keuls test. Values of $P<0.05$ were considered significant (*).

Results hES cells expressed mRNA transcripts for three S1P receptors: $S1P_1$, $S1P_2$ and $S1P_3$ and for each of the LPA receptors (FIG. 4A-B). However these cells did not express mRNA for $S1P_4$ and $S1P_5$. Contrary to mouse embryonic stem cells, hES cells expressed mRNA transcripts for PDGFR-α and PDGFR-β (FIG. 4C) as well as the corresponding proteins, as revealed by immunostaining (FIG. 4E-J). As previously shown by others[6-8,18,19], we show that MEF expressed $S1P_1$, $S1P_2$, $S1P_3$, $LPA_1$, $LPA_2$, PDGFR-α and PDGFR-β. Thus in a co-culture system, S1P, LPA and PDGF could be active on either cell type.

We next examined whether S1P, LPA and PDGF could affect growth or differentiation of hES cells. When hES cells were grown on MEF in a serum-free culture medium, they spontaneously differentiated into different kinds of cells. After 2 weeks in a serum-free media, LPA (up to 50 μM) had no obvious effect on size or morphology of hES cell colonies whilst in the presence of either S1P (10 μM) or PDGF-AB (PDGF, 20 ng/ml), the colonies appeared flatter and less differentiated as compared to the controls. Moreover, the co-incubation of S1P and PDGF induced a strong inhibition of spontaneous differentiation. To quantify these effects, we used an ELISA-based assay to measure expression of the stem cell surface antigen GCMT-2 (GCTM2+) in cells treated for 2 weeks with different agonists. Thus, cells treated with S1P or PDGF were respectively 18.0±17.0% (n=3) and 50.3±18.4% (n=3) more GCMT2+ than the controls and the ones treated with both S1P and PDGF were 152.7±54.9% (n=3) more GCTM2+ than the controls (FIG. 5A). Using the same technique, we showed that cells treated with S1P and either PDGF-AA or PDGF-BB showed a GCTM2 expression similar to the one observed with S1P and PDGF (PDGF-BB: 294.3±77.3% of control, n=3, PDGF-AA: 220.3±49.0% of control, n=3; FIG. 5A). Moreover, the effect of S1P in combination with PDGF was mimicked by the use of dihydrosphingosine-1-phosphate (dihydro-S1P, 10 mM), a S1P analogue that mimics its receptor-dependent effects, in combination with PDGF (227.0±59.9% of control (n=3), FIG. 5A). Furthermore, dihydro-S1P on its own had a more potent effect on hES cells than S1P (223.0±27.0% of control, n=3; FIG. 5A). Together, these results suggest that the combination of PDGF and S1P in a serum-free culture medium prevents the spontaneous differentiation of hES cells. This effect is dependent upon S1P's receptors and both PDGFRs, as PDGF-AA only binds to PDGFR-α while PDGF-AB and PDGF-BB bind to both receptors. Moreover, treatment of hES cells with the MAP kinase kinase inhibitor U0126 (Promega, 10 mM) for 7 days, totally inhibited the effect of PDGF and S1P on GCTM2 expression (FIG. 5B), strongly suggesting that the activation of the extracellular signal-regulated kinases is required to maintain hES cells undifferentiated. As SPK is a key molecule in PDGF signalling pathways, we verified the presence of SPK transcripts in hES cells and showed expression of both SPK-1 and SPK-2 mRNA (FIG. 4D). We next investigated if PDGF modulates SPK activity in hES cells (FIG. 5D). PDGF (20 ng/ml) enhanced in a time-dependent manner the SPK activity in hES cells (FIG. 5D). This effect lasted for at least 60 min and SPK activity reached 1.6 fold the basal values (75.3±3.92 nmol/min/mg, n=3) after 30 min of incubation (FIG. 5D). In contrast, PDGF (20 ng/ml) did not induce a significant statistical activation of SPK in MEF. Moreover, treatment of hES cells with dimethylsphingosine (DMS, 3 □M, FIG. 5C), a non-specific inhibitor of SPK, for 7 days, inhibited the effect of PDGF and S1P, suggesting an involvement of SPK in the maintenance of hES in an undifferentiated state.

To date, hES cells have been grown in a serum-free medium supplemented with S1P (10 μM) and PDGF (20 ng/ml) for 19 passages. As these cells still express SPK-1 and SPK-2 mRNA (FIG. 6B), we can expect the PDGF-activation of SPK to be involved in the propagation of hES cells. RT-PCR studies showed that hES cells expressed the mRNA for Oct-4 and cripto (FIG. 6B), and immunostaining showed immunoreactivity to the stem cell markers GCTM-2, Oct-4, TG-30 and Tra-1-60 (FIG. 6C-F). These hES cells retained a normal karyotype (FIG. 6G). Moreover, these HES cells still responded to noggin treatment and were able to form neurospheres (FIG. 6H) and neuronal cells as ascertained by immunostaining for βtubulin (FIG. 6I), Map2, nestin, synaptophysin, N-cam and NF200 (Pera et al submitted). Altogether, these data demonstrate that HES cells grown in the presence of S1P and PDGF retain the characteristics of HES cells propagated in normal serum conditions.

Discussion

In this study, we show for the first time that hES cells are targets of S1P, LPA and PDGF and we also show an interaction between S1P and PDGF signal, in that extracellular S1P and PDGF need to be present together to exert a potent biological effect. Katsuma et al. (2002)[17] reported a similar mechanism in mesangial cells where application of S1P and PDGF increases proliferation. In hES cells the addition of both S1P and PDGF maintains these cells in the undifferentiated state, and still allows them to follow differentiation. These combined effects could be attributed to the fact that (i) S1P acts extracellularly through its receptors to modulate intracellular signalling pathways; (ii) and that PDGF stimulates the formation of intracellular S1P which would either be secreted or act as an intracellular messenger, for instance in the regulation of calcium homeostasis[13] and in the suppression of apoptosis, as shown in fibroblasts[14] and other cell types[15,16]. Whether S1P is secreted or acts as a second messenger needs to be further investigated. However, because the maintenance of hES cells in an undifferentiated state only occurs in the presence of both PDGF and S1P, we could expect that intracellular S1P, produced in response to PDGF, acts within the cells, as its cell-surface receptors are likely to have already been engaged by S1P previously added to the culture media. To our knowledge, this study is the first one to report a cross-talk involving S1P and two isoforms of PDGFR, instead of only PDGFR-β. These data demonstrate that S1P and PDGF are key elements in the regulation of spontaneous differentiation of hES cells. Their identification as compounds having an ability to inhibit differentiation allows the design of a simple serum-free culture medium more suitable for hES cell propagation.

The following materials and methods relate to Examples 3 to 5.

Reagents

S1P AND LPA were obtained from Biomol (Plymouth Meeting, Pa., USA) and were dissolved in methanol. Freshly prepared dilutions of agonists were made in water containing 0.1% fatty acid-free bovine serum albumin (BSA) (Sigma). Protease, sodium orthovanadate and U0126 were from Sigma. was from Calbiochem (San Diego, Calif., USA). *Pertussis* Toxin (PTX) was from List Biological Laboratories (Campbell, Calif., USA). GCTM-2, Oct-4, PCNA, Hoechst-33342

Cell Culture hES-3 cells were cultured as previously described [1]. Human stem cells were grown on MMC treated fibroblasts' feeder layer. Fibroblasts were plated on gelatine treated dishes. A combination of human and mouse derived fibroblasts were used at a density of approximately 25,000 and 70,000 cells per cm2 respectively. The fibroblasts were plated up to 48 hours before culture of the stem cells. Mouse fibroblasts only could also support the growth of the stem cells. However, while human fibroblasts could also support stem cells, they created an uneven and unstable feeder layer. Therefore, the human fibroblasts were combined with the mouse fibroblasts to augment and achieve better support of growth and prevention of differentiation.

The medium that was used for the growth of human stem was DMEM (GIBCO, without sodium pyruvate, with glucose 4500 mg/L) supplemented with 20% FBS (Hyclone, Utah) (2-mercaptoethanol-0.1 mM (GIBCO), Non Essential Amino Acids—NEAA 1% (GIBCO), glutamine 2 mM. (GIBCO), penicillin 50 u/ml, and streptomycin 50 mg/ml (GIBCO)

For direct observation, hES-3 cells were coated into 12-well plates (3 colonies per well), with or without mouse embryonic feeders (MEFs). The day following the plating, cells were incubated with the different agents in serum free medium containing insulin, transferring and selenium. Media was changed the $2^{nd}$ day and then every 2 days.

For immunostaining, hES-3 cells were coated on chamber slides after mechanical dissociation, in order to obtain a monolayer culture. The day following the plating, cells were incubated with the different agents in a media depleted in serum. Media was changed the $2^{nd}$ day and the cells were fixed 4 days after the first treatment.

For immunoblot analysis, cells were transferred into 24 well plates (8 colonies per well) without MEFs, and 24 hr later, were grown in the absence of serum for 18 hrs.

In some experiments, cells were pre-treated for 1 hr with U0126 (30 μM) or for 18 hrs with PTX (100 μg/ml).

RT-PCR Experiments

Cells were washed with PBS and hES colonies were removed by treatment with protease. Purified mRNA was extracted from hES cultures using Dynabeads® Oligo (dT)$_{25}$ (Dynal, Oslo, Norway), according to the supplier's instruction. RT was performed using Superscript™ II Rnase H⁻ Reverse Transcriptase (Invitrogen, Life technologies), according to the supplier's protocol. After cooling on ice, the cDNA samples were amplified by PCR with sense and antigens primers (synthesis performed by Sigma Genosys, Castle Hill, Australia) designed for the specific detection of human Edg-1, Edg-2, Edg-3, Edg-4, Edg-5, Edg-6, Edg-7 and Edg-8 DNA target sequences. The primers used for Edg-1, Edg-3, Edg-5, Edg-6 and Edg-8 were previously designed by Hornu et al. (2001) [1]. These primer pairs were:

```
5'-CCACAACGGGAGCAATAACT-3'  (sense, SEQ ID NO:29) and

5'-GTAAATGATGGGGTTGGTGC-3'  (antisense, SEQ ID NO:30) (expected PCR product: 480 bp) for Edg-1;

5'-TCAGGGAGGGCAGTATGTTC-3'  (sense, SEQ ID NO:31) and

5'-CTGAGCCTTGAAGAGGATGG-3'  (antisense, SEQ ID NO:32) (505 bp) for Edg-3;

5'-CCAATACCTTGCTCTCTCTGGC-3' (sense, SEQ ID NO:33) and

5'-CAGAAGGAGGATGCTGAAGG-3'  (antisense, SEQ ID NO:34) (502 bp) for Edg-5;

5'-CGGCTCATTGTTCTGCACTA-3'  (sense, SEQ ID NO:35) and

5'-GATCATCAGCACCGTCTTCA-3'  (antisense, SEQ ID NO:36) (701 bp) for Edg-6;

5'-TTCTGATACCAGAGTCCGGG-3'  (sense, SEQ ID NO:37) and

5'-CAAGGCCTACGTGCTCTTCT-3'  (antisense, SEQ ID NO:38) (460 bp) for Edg-8.
```

-continued

For Edg-2 and Edg-4, the primer pairs designed by Goetzl et al. (1999) were used:
5'-GCTCCACACACGGATGAGCAACC-3' (sense, SEQ ID NO:39) and 5'-GTGGTCATTGCTGTGAACTCCAGC-3' (antisense, SEQ ID NO:40) (621 bp) for Edg-2, 5'-AGCTGCACAGCCGCCTGCCCCGT-3' (sense, SEQ ID NO:41) and 5'-TGCTGTGCCATGCCAGACCTTGTC-3' (antisense, SEQ ID NO:42) (775 bp) for Edg-4.

For Edg-7, the primer pairs designed by Goetlz et al. (2000) were used:
5'-CCATAGCAACCTGACCAAAAAGAG-3' (sense, SEQ ID NO:43) and 5'-TCCTTGTAGGAGTAGATGATGGGG-3' (antisense, SEQ ID NO:44) (482 bp).

For Edg-7, the primer pairs designed by Goetlz et al. (2000) were used:

```
5'-CCATAGCAAACCTGACCAAAAAGAG-3' (sense) and
5'-TCCTTGTAGGAGTAGATGATGGGG-3' (antisense)
(482 bp).
```

PCR experiments were performed in a mixture (25 µl) containing 0.25 units of Taq DNA polymerase (Biotech International Ltd, Perth, WA, Australia) and 2 µM of each primer in a buffer including 67 mM Tris-HCl pH 8.8, 1.5 mM $MgCl_2$, 16.6 mM $[NH_4]_2SO_4$, 0.45% Triton X-100, 0.25 mM of each dATP, dGTP, dCTP, dTTP. Absence of contaminating genomic DNA was confirmed by control reactions with mRNA that had not been treated with reverse transcriptase. PCR experiments were run with the following steps: initial denaturation at 94° C. for 5 min, 35 cycles of denaturation at 94° C. for 30 sec, annealing at 52° C. (Edg-1, Edg-3, Edg-5, Edg-6, Edg-8) or 56° C. (Edg-2, Edg-4, Edg-7) for 2 min, extension at 74° C. for 2 min, and a final extension at 74° C. for 7 min. The specific amplified DNA fragments were purified by electrophoresis on 1.5% (w/v) agarose gel, stained with ethidium bromide and photographed. The amplicons were purified and sequenced.

Immunofluorescence

Cells were washed in PBS, fixed with MeOH, and immunostaining was performed, using the specific stem cell marker antibody GCTM-2, and the specific cell proliferation marker PCNA. Cells were then washed and the nucleuses were stained with Hoechst-33342 (1 µg/ml). Slides were mounted and then observed by fluorescent microscopy. Cells were then counted in order to determine the ratio of proliferating stem cells within the overall population.

Western Blot Analysis hES3 cells were lysed following removal of the supernatants by addition of a reducing loading buffer (2% SDS, 62.5 mM Tris pH 6.8, 0.1 M DTT, 0.01% bromophenol blue) containing 1 mM sodium orthovanadate. Samples were boiled for 10 min and centrifuged at 13000 g for 15 min, and protein lysates (approx. 80 µg) were separated by SDS-polyacrylamide gel electrophoresis (10% polyacrylamide, w/v). Proteins were transferred to nitrocellulose (Hybond-ECL, Amersham) and immunoblotting was carried out with rabbit polyclonal anti-active mitogen-activated protein (MAPK) antibodies raised against a dually phosphorylated MAPK peptide (Promega, Madison, Wis., USA). Peroxidase-coupled secondary antibody (Dako) was detected by exposure of autoradiographic films in the presence of a chemiluminescent detection reagent (ECL, Amersham). Stripping of antibodies was achieved by incubating the membrane during 30 min at 50° C. in a buffer containing 100 mM mercaptoethanol, 2% SDS, 62.5 mM Tris-HCl pH 6.7. The membrane was then reprobing with rabbit polyclonal anti-ERK1/2 antibodies (Promega), and then with peroxidase-coupled secondary antibodies (Dako).

Blots probed with either rabbit polyclonal anti-active p38 (Promega) or rabbit polyclonal anti-active JNK (Promega) or mouse polyclonal GCTM-2 antibodies were also performed, using the same procedure as described above.

Protein Quantification hES3 cells were lysed and their quantity was determined by using a calorimetric assay based on the Bradford dye-binding test (Bio-Rad Laboratories, Regents Park, NSW, Australia).

Each set of experiments was performed at least 3 times (n refers to number of independent experiments performed on different cell cultures).

Example 3

The results presented in FIG. 7A indicate that hES cells expressed mRNA transcripts for the three S1P receptors: Edg-1, Edg-3 and Edg-5 while these cells do not seem to express mRNA for Edg-6 and Edg-8 (data not shown). Moreover, hES cells express mRNA transcripts for each of LPA receptors: Edg-2, Edg-4 and Edg-7 (FIG. 7B). The nucleotide sequences of all purified PCR products were analysed and revealed to be identical to the corresponding regions in the human receptor genes.

Example 4

Applicants next determined whether S1P could modulate the fate of hES cells. When hES cells were grown on MEFs, in a culture media depleted in serum, they spontaneously differentiated. As shown in FIG. 8, after 8 days in such conditions, hES cells colonies contained enlarged flattened cells which formed cystic structures (FIGS. 2A, 2B). Even after 12 days, LPA (up to 50 µM) did not seem to affect the growth of the colonies (data not shown). In presence of S1P (10 µM, 8 days), the colonies were more compact and less differentiated than in the control condition (FIG. 8C). This effect of S1P was more obvious after 12 days of treatment (FIGS. 8D, 8E). The inhibitory effect of S1P on cell differentiation and the lack of effect of LPA were also observed when hES cells were grown without MEFs, suggesting that S1P did not directly act on the feeder cells (n=3, data not shown).

In order to understand and quantify the effect of S1P on the spontaneous differentiation of hES cells, double immunostaining experiments were carried out. For that purpose, Applicants used two specific antibodies, one as a stem cell marker, GCTM-2, and one for proliferation, PCNA, a marker that is only expressed during the S phase of the cell cycle, in order to determine the ratio of proliferating stem cells (FIG. 9). After 4 days in a media without serum, most of the control cells were differentiated (FIGS. 9A, 9C and 9E), as revealed by the fact that only 16% of the cells still expressed GCTM-2 (FIG. 10A). By contrast, when S1P (10 µM) was added to the media, 68% of the cells were GCTM-2 positive, suggesting that most of the cells remained stem cells (FIGS. 9B, 9D, 9F and 10B). Within these cell populations, a large part expressed PCNA, suggesting that most of these stem cells still proliferated (FIGS. 9G and 9H). However, no marked difference in the proliferating rate of hES cells between the control cells and the ones treated with S1P were observed (FIG. 10). Altogether, these data suggest that S1P mostly acts on the differentiation of hES cells observed in absence of serum rather then acts on the proliferating state of hES cells.

Example 5

Because the MAP kinases ERKs have often been implicated in cell proliferation and differentiation, the effects of S1P on the activation of the ERKs were then investigated. After 5 min, S1P stimulated the phosphorylation of ERKs in hES cells (FIG. 10), an effect that was totally inhibited in presence of the MEK inhibitor U0126 (30 µM) (FIG. 10A). S1P stimulated ERKs for at least 60 min and in a concentration dependant manner (FIG. 10B, 10C).

These results show clearly that treatment of human ES cells with S1P results in inhibition of spontaneous differentiation. S1P is a major component of serum, and is therefore likely to account for much of the beneficial effect of calf serum in human ES cultures. Although human ES cells express receptors for both S1P and LPA, the latter lysophospholipid is inactive on human ES cells. This suggests that particular members of the Edg receptor family have distinct effects on human ES cell behaviour.

REFERENCES

1. Reubinoff, B. E., Pera, M. F., Fong, C. Y., Trounson, A. & Bongso, A. Embryonic stem cell lines from human blastocysts: somatic differentiation in vitro. *Nat Biotechnol* 18, 399-404 (2000).
2. Homuss, C., Hammermann, R., Fuhrmann, M., Juergens, U. R. & Racke, K. Human and rat alveolar macrophages express multiple EDG receptors. *Eur J Pharmacol* 429, 303-8 (2001).
3. Goetzl, E. J., Dolezalova, H., Kong, Y. & Zeng, L. Dual mechanisms for lysophospholipid induction of proliferation of human breast carcinoma cells. *Cancer Res* 59, 4732-7 (1999).
4. Basciani, S. et al. Expression of platelet-derived growth factor-A (PDGF-A), PDGF-B, and PDGF receptor-alpha and -beta during human testicular development and disease. *J Clin Endocrinol Metab* 87, 2310-9 (2002).
5. van Eijk, M. J. et al. Molecular cloning, genetic mapping, and developmental expression of bovine POU5F1. *Biol Reprod* 60, 1093-103 (1999).
6. Rosenfeldt, H. M., Hobson, J. P., Milstien, S. & Spiegel, S. The sphingosine-1-phosphate receptor EDG-1 is essential for platelet-derived growth factor-induced cell motility. *Biochem Soc Trans* 29, 836-9 (2001).
7. Ishii, I. et al. Selective loss of sphingosine 1-phosphate signaling with no obvious phenotypic abnormality in mice lacking its G protein-coupled receptor, LP(B3)/EDG-3. *J Biol Chem* 276, 33697-704 (2001).
8. Heldin, C. H. & Westermark, B. Mechanism of action and in vivo role of platelet-derived growth factor. *Physiol Rev* 79, 1283-316 (1999).
9. Takuwa, Y., Takuwa, N. & Sugimoto, N. The edg family g protein-coupled receptors for lysophospholipids: their signaling properties and biological activities. *J Biochem* (Tokyo) 131, 767-71 (2002).
10. Chun, J. et al. International Union of Pharmacology. XXXIV. Lysophospholipid Receptor Nomenclature. *Pharmacol Rev* 54, 265-9 (2002).
11. Graler, M. H., Bernhardt, G. & Lipp, M. EDG6, a novel G-protein-coupled receptor related to receptors for bioactive lysophospholipids, is specifically expressed in lymphoid tissue. *Genomics* 53, 164-9 (1998).
12. Im, D. S. et al. Characterization of a novel sphingosine 1-phosphate receptor, Edg-8. *J Biol Chem* 275, 14281-6 (2000).
13. Mattie, M., Brooker, G. & Spiegel, S. Sphingosine-1-phosphate, a putative second messenger, mobilizes calcium from internal stores via an inositol trisphosphate-independent pathway. *J Biol Chem* 269, 3181-8 (1994).
14. Cuvillier, O. et al. Suppression of ceramide-mediated programmed cell death by sphingosine-1-phosphate. *Nature* 381, 800-3 (1996).
15. Van Brocklyn, J. R. et al. Dual actions of sphingosine-1-phosphate: extracellular through the Gi-coupled receptor Edg-1 and intracellular to regulate proliferation and survival. *J Cell Biol* 142, 229-40 (1998).
16. Olivera, A. et al. Sphingosine kinase expression increases intracellular sphingosine-1-phosphate and promotes cell growth and survival. *J Cell Biol* 147, 545-58 (1999).
17. Katsuma, S. et al. Signalling mechanisms in sphingosine 1-phosphate-promoted mesangial cell proliferation. *Genes Cells* 7, 1217-30 (2002).
18. Pebay, A. et al. Sphingosine-1-phosphate induces proliferation of astrocytes: regulation by intracellular signalling cascades. *Eur J Neurosci* 13, 2067-76 (2001).
19. Pitson, S. M. et al. Human sphingosine kinase: purification, molecular cloning and characterization of the native and recombinant enzymes. *Biochem J* 350 Pt 2, 42941 (2000).
20. Andrews, P. W. et al. Comparative analysis of cell surface antigens expressed by cell lines derived from human germ cell tumours. *Int J Cancer* 66, 806-16 (1996).
21. Baron, V. & Schwartz, M. Cell adhesion regulates ubiquitin-mediated degradation of the platelet-derived growth factor receptor beta. *J Biol Chem* 275, 39318-23 (2000).
22. Kluk, M. J., Colmont, C., Wu, M. T. & Hla, T. Platelet-derived growth factor (PDGF)-induced chemotaxis does not require the G protein-coupled receptor S1P(1) in murine embryonic fibroblasts and vascular smooth muscle cells. *FEBS Lett* 533, 25-8 (2003).

The invention claimed is:

1. A serum free or substantially serum free medium useful for modulating spontaneous differentiation of a stem cell, comprising an agonist of the LPL receptor and a ligand of a class III tyrosine kinase receptor, wherein the agonist is selected from the group consisting of S1P, dihydro-S1P, LPA, PAF and SPC.

2. A medium according to claim 1 wherein the modulation is inhibition of differentiation.

3. A medium according to claim 1 wherein the medium is serum free.

4. A medium according to claim 1 wherein the LPL receptor is selected from the group consisting of S1P1, S1P2, and S1P3.

5. A medium according to claim 1 wherein the agonist is S1P.

6. A medium according to claim 1 wherein the agonist is dihydro S1P.

7. A medium according to claim 1 comprising TNF alpha, NGF (nerve growth factor), a muscarinic acetylcholine agonist, a serum or phorbol ester.

8. A medium according to claim 1 wherein the stem cell is derived from foetal tissue or adult tissue.

9. A medium according to claim 8 wherein the stem cell is an ES cell.

10. A medium according to claim 8 wherein the stem cell is a hES cell.

11. A medium according to claim 1 wherein the base medium is a standard serum free medium.

12. A medium according to claim 1 comprising 25 mM Hepes.

13. A medium according to claim 11 wherein the base medium is based on DMEM supplemented with insulin, transferrin and selenium.

14. A medium according to claim 1 wherein the agonist is S1P and is present in the medium at a concentration of from 0.1 µM to 10 µM.

15. A medium according to claim 1 wherein the agonist is present in the medium at a concentration of about 10 µM.

16. A medium according to claim 1 wherein the tyrosine kinase receptor is PDGFR-α or PDGFR-β.

17. A medium according to claim 1 wherein the ligand is a PDGF or a functional equivalent thereof.

18. A medium according to claim 17 wherein the PDGF is PDGFaa, PDGFab or PDGFbb.

19. A serum-free or substantially serum-free medium useful for modulating spontaneous differentiation of a stem cell, comprising an agonist of a LPL receptor wherein said agonist is PAF.

20. A medium according to claim 19 wherein the modulation is inhibition of differentiation.

21. A medium according to claim 19 wherein the medium is serum free.

22. A medium according to claim 19 wherein the base medium is a standard serum free medium.

23. A medium according to claim 19 comprising 25 mM Hepes.

24. A medium according to claim 22 wherein the base medium is based on DMEM supplemented with insulin, transferring and selenium.

25. A medium according to claim 19 wherein the agonist is present in the medium at a concentration of about 10 μM.

* * * * *